United States Patent
Bakshi et al.

[11] Patent Number: 5,998,464
[45] Date of Patent: Dec. 7, 1999

[54] 4-OXA AND 4-THIA STEROIDS

[75] Inventors: Raman K. Bakshi, Edison; Gool F. Patel, Califon; Gary H. Rasmusson, Watchung; Richard L. Tolman, Warren, all of N.J.

[73] Assignee: Merck & Co., Inc., Rahway, N.J.

[21] Appl. No.: 09/065,112

[22] PCT Filed: Oct. 22, 1996

[86] PCT No.: PCT/US96/16883

§ 371 Date: Apr. 23, 1998

§ 102(e) Date: Apr. 23, 1998

[87] PCT Pub. No.: WO97/15564

PCT Pub. Date: May 1, 1997

Related U.S. Application Data

[60] Provisional application No. 60/006,001, Oct. 26, 1995.

[51] Int. Cl.$^6$ .................. A61K 31/35; A61K 31/38; C07D 311/78; C07D 311/94; C07D 335/04
[52] U.S. Cl. .................. 514/432; 514/36; 514/253; 514/254; 514/256; 514/324; 514/337; 514/414; 514/422; 514/453; 544/229; 544/335; 544/375; 546/14; 546/19; 546/280.1; 548/110; 548/467; 548/525; 549/4; 549/25; 549/383
[58] Field of Search .................. 514/63, 253, 254, 514/256, 324, 337, 414, 422, 432, 453; 544/229, 335, 375; 546/14, 196, 280.1; 548/110, 467, 525; 549/4, 25, 383

[56] References Cited

U.S. PATENT DOCUMENTS

| | | | |
|---|---|---|---|
| 3,644,421 | 2/1972 | Cross | 260/340.5 |
| 4,760,071 | 7/1988 | Rasmusson et al. | 514/284 |
| 5,075,450 | 12/1991 | Rasmusson et al. | 546/285 |
| 5,084,574 | 1/1992 | Bhattacharya et al. | 546/77 |
| 5,091,380 | 2/1992 | Rasmusson et al. | 514/169 |

FOREIGN PATENT DOCUMENTS

WO 96/20713  7/1996  WIPO .

OTHER PUBLICATIONS

Wall Street Journal, May 7, 1996, p. B4, "Study finds Abbott's prostate drug is much more effective than Merck's".

The Daily, Tuesday, May 7, 1996, "New data on Proscar, Abbott's Hytrin show conflicting results".

Tian et al., Biochemistry, vol. 33 (1994), pp. 2291–2296, "17beta-(N-tert-butylcarbmoyl)-4-aza-5alpha-androstan-1-en-3-one is an active site-directed slow time-dependent . . . ".

Everse et al., Bioorganic Chemistry, vol. 1 (1971), pp. 207–233, "Addition products of diphosphopyridine nucleotides with substracts of pyridine nucleotide–linked dehydrogenases".

Bull et al., J. Am. Chem. Soc., vol. 118 (1996), pp. 2359–2365, "Mechanism–based inhibition of human steroid 5alpha–reductase by finasteride".

Faller et al., Biochemistry, vol. 32 (1993), pp. 5705–5710, "Finasteride: A slow–binding 5alpha–reductase inhibitor".

Baginsky et al., FASEB J., vol. 8 (1994), p. 638, "Mechanism of inhibition of human prostatic 5alpha–reductase by 4–azasteroids".

Barton et al., J. of the Chem. Soc., Perkin Trans. 1, No. 8 (1982), pp. 1919–1922, "Dehydrogenation of lactones using benzeneseleninic ahydride".

Barton et al., Tetrahedron Letters, No. 35 (1979), pp. 3331–3334, "Preparation of aldehydes and ketones by oxidation of benzylic hydrocarbons with benzeneseleninic anhydride".

Canovas et al., Helv. Chmi. Acta., vol. 63(8), pp. 2390–2392 (1980), "253. A Norrish Type I cleavage in the photolysis of a steroidal alpha, beta–unsaturated gamma–lactone".

Caspi et al., Tetrahedron, vol. 18, pp. 1013–1018 (1962), "Ozonolysis of conjugated systems–II . . . ".

Primary Examiner—Richard L. Raymond
Assistant Examiner—Brenda Coleman
Attorney, Agent, or Firm—Catherine D. Fitch; Melvin Winokur

[57] ABSTRACT

The compounds of the present invention are those of structural formula (I)

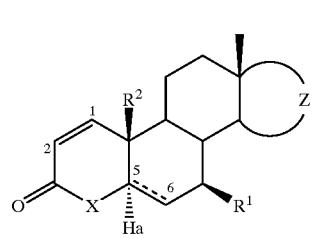

wherein X is oxygen or sulfur. Pharmaceutical compositions and methods of use of the compounds in the treatment of hyperandrogenic conditions are disclosed. In addition, the combination of the compounds with other active agents such as finasteride, minoxidil and retinoic acid or a derivative thereof is disclosed.

14 Claims, No Drawings

4-OXA AND 4-THIA STEROIDS

CROSS REFERENCE TO RELATED APPLICATIONS

The present application is the national phase application under 35 U.S.C. §371 of PCT application Serial No. PCT/US96/16883, filed Oct. 22, 1996, based on provisional application 60/006,001, filed Oct. 26, 1995.

FIELD OF THE INVENTION

The present invention provides novel compounds, novel compositions, methods of their use and methods of their manufacture, where such compounds are generally pharmacologically useful as agents in therapies whose mechanism of action rely on the inhibition of 5α-reductase.

BACKGROUND OF THE INVENTION

Certain undesirable physiological manifestations, such as acne vulgaris, seborrhea, female hirsutism, androgenic alopecia which includes female and male pattern baldness, and benign prostatic hyperplasia, are the result of hyperandrogenic stimulation caused by excessive accumulation of testosterone ("T") or similar androgenic hormones in the metabolic system. Androgenic alopecia is also known as androgenetic alopecia. Early attempts to provide a chemotherapeutic agent to counter the undesirable results of hyperandrogenicity resulted in the discovery of several steroidal antiandrogens having undesirable hormonal activities of their own. The estrogens, for example, not only counteract the effect of the androgens but have a feminizing effect as well. Non-steroidal antiandrogens have also been developed, for example, 4'-nitro-3'-trifluoromethyl-isobutyranilide. See Neri, et al., Endocrinol. 1972, 91 (2). However, these products, though devoid of hormonal effects, compete with all natural androgens for receptor sites, and hence have a tendency to feminize a male host or the male fetus of a female host and/or initiate feed-back effects which would cause hyperstimulation of the testes.

The principal mediator of androgenic activity in some target organs, e.g. the prostate, is 5α-dihydrotestosterone ("DHT"), formed locally in the target organ by the action of testosterone-5α-reductase. Inhibitors of testosterone-5α-reductase will serve to prevent or lessen symptoms of hyperandrogenic stimulation in these organs. See especially U.S. Pat. No. 4,377,584, issued Mar. 22, 1983, and U.S. Pat. No. 4,760,071, issued Jul. 26, 1988, both assigned to Merck & Co., Inc.

The enzyme 5α-reductase catalyzes the reduction of testosterone to the more potent androgen, dihydrotestosterone, as shown below:

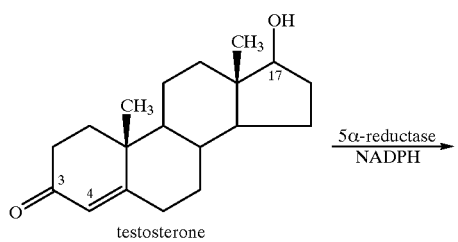

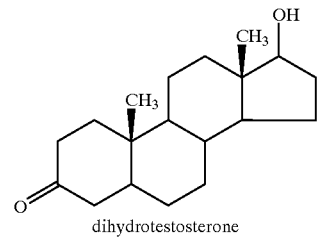

Finasteride, (17β-(N-tert-butylcarbamoyl)-3-oxo-4-aza-5α-androst-1-ene-3-one) as shown below, is a potent inhibitor of the human prostate enzyme.

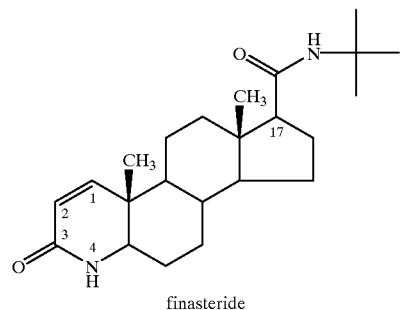

Under the trade name PROSCAR®, finasteride is known to be useful in the treatment of hyperandrogenic conditions; see eg. U.S. Pat. No. 4,760,071. Finasteride is currently prescribed for the treatment of benign prostatic hyperplasia (BPH), a condition afflicting to some degree the majority of men over age 55. Finasteride's utility in the treatment of androgenic alopecia and prostatic carcinoma is also disclosed in the following documents: EP 0 285,382, published Oct. 5, 1988; EP 0 285,383, published Oct. 5, 1988; Canadian Patent no. 1,302,277; and Canadian Patent no. 1,302,276.

There are two isozymes of 5α-reductase in humans. One isozyme (type 1 or 5α-reductase 1) predominates in sebaceous glands of facial and skin tissue and is relatively insensitive to finasteride (see, e.g., G. Harris, et al., Proc. Natl. Acad. Sci. USA, Vol. 89, pp. 10787–10791 (November 1992)); the other (type 2 or 5α-reductase 2) predominates in the prostate and is potently inhibited by finasteride.

Since 5α-reductase and its isozymes convert testosterone to DHT, inhibition of either or both of the isozymes would serve to alleviate the conditions and diseases mediated by DHT. The present invention addresses this by providing novel compounds that are active as inhibitors of 5α-reductase.

SUMMARY OF THE INVENTION

The novel compounds of the present invention are those of structural formula I:

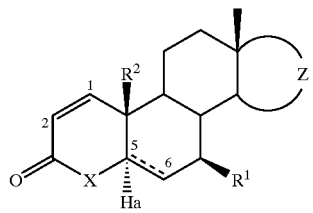

(I)

wherein X is selected from O and S,
or a pharmaceutically acceptable salt, ester, or stereoisomer thereof, and are inhibitors of 5α-reductase. The compounds of formula I are useful in the oral, systemic, parenteral or topical treatment of hyperandrogenic conditions such as acne vulgaris, seborrhea, androgenic alopecia which includes female and male pattern baldness, female hirsutism, benign prostatic hyperplasia, and the prevention and treatment of prostatic carcinoma, as well as in the treatment of prostatitis.

Therefore it is an object of this invention to provide compounds that have sufficient activity in the inhibition of 5α-reductase. It is an additional object of this invention to provide methods of using the compounds of formula I for the treatment of hyperandrogenic conditions such as acne vulgaris, seborrhea, androgenic alopecia, male pattern baldness, female hirsutism, benign prostatic hyperplasia, and the prevention and treatment of prostatic carcinoma, as well as the treatment of prostatitis. It is a further object of this invention to provide pharmaceutical compositions for the compounds of formula I. Another object of this invention is to provide compounds of formula I in combination with other active agents, for example with finasteride, or a potassium channel opener, such as minoxidil, or a retinoic acid or a derivative thereof, wherein such combinations would be useful in one or more of the above-mentioned methods of treatment or pharmaceutical compositions.

DETAILED DESCRIPTION OF THE INVENTION

The novel compounds of this invention have the structural formula I:

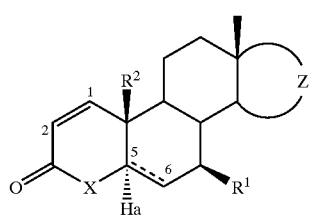

(I)

or a pharmaceutically acceptable salt, ester or stereoisomer thereof, wherein:

the C5–C6 bond designated with a dotted line independently represents a single or double bond, provided that when the C5–C6 is a double bond, $H_a$ is absent and when the C5–C6 bond is a single bond $H_a$ is present and represents hydrogen;

X is selected from oxygen and sulfur;

$R^1$ is selected from hydrogen and $C_{1-5}$ alkyl;

$R^2$ is selected from $CH_3$, $CH_2OR^3$, and H;

$R^3$ is selected from: $C_{1-5}$ alkyl;

Z is

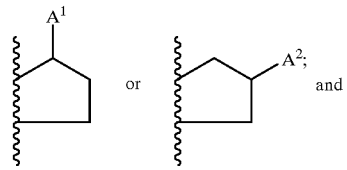

$A^1$ is selected from:
(1) —H,
(2) keto,
(6) carboxy,
(7) protected amino,
(8) amino,
(9) $C_{1-10}$alkyl,
(10) substituted or unsubstituted $C_{2-10}$alkenyl,
(11) aryl-substituted $C_{1-10}$ alkyl,
(12) aryl or heteroaryl,
(13) substituted aryl or heteroaryl,
(14) aryl or heteroaryl carbamoyl-substituted $C_{1-10}$alkyl,
(15) $C_{1-10}$alkylcarbonyl,
(16) aryl or heteroaryl carbonyl,
(17) ether-substituted $C_{1-10}$alkyl,
(18) thioether-substituted $C_{1-10}$alkyl,
(19) keto-substituted $C_{1-10}$ alkyl,
(20) heteroaryl-substituted $C_{1-10}$ alkyl,
(21) carboxylic ester,
(22) carboxamide, including substituted and unsubstituted anilide derivatives,
(23) urea,
(24) $C_{1-10}$ alkylureido $C_{0-5}$ alkyl,
(25) substituted or unsubstituted heteroaryl or arylureido$C_{0-5}$ alkyl,
(26) $C_{1-10}$alkanoyloxy$C_{1-2}$alkyl,
(27) $C_{1-10}$ alkylcarbonylamino,
(28) alkanoylamidoalkyl
(29) ether,
(30) thio ether, and
(31) substituted and unsubstituted aryl or heteroaryl ether;

$A^2$ is selected from:
(1) —H,
(2) keto,
(3) protected hydroxy,
(4) acetate,
(5) hydroxy,
(6) carboxy,
(7) protected amino,
(8) amino,
(9) $C_{1-}$ alkyl,
(10) substituted or unsubstituted $C_{2-10}$alkenyl,
(11) aryl-substituted $C_{1-10}$ alkyl,
(12) aryl or heteroaryl,
(13) substituted aryl or heteroaryl,
(14) aryl or heteroaryl carbamoyl-substituted $C_{1-10}$alkyl,
(15) $C_{1-10}$alkylcarbonyl,
(16) aryl or heteroaryl carbonyl,
(17) ether-substituted $C_{1-10}$alkyl,
(18) thioether-substituted $C_{1-10}$alkyl,
(19) keto-substituted $C_{1-10}$alkyl,
(20) heteroaryl-substituted $C_{1-10}$ alkyl,
(21) carboxylic ester,
(22) carboxamide, including substituted and unsubstituted anilide derivatives,

(23) urea,
(24) C$_{1-10}$ alkylureido C$_{0-5}$ alkyl,
(25) substituted or unsubstituted arylureidoC$_{0-5}$ alkyl,
(26) C$_{1-10}$alkanoyloxyC$_{1-2}$alkyl,
(27) C$_{1-10}$ alkylcarbonylamino,
(28) alkanoylamidoalkyl,
(29) ether,
(30) thio ether, and
(31) substituted and unsubstituted aryl- or heteroaryl-ether;

Heteroaryl is selected from piperidinyl, piperizinyl, pyrrolidinyl, pyrrolyl, furanyl, thienyl, pyridyl, pyrimidinyl, indolyl and benzofuranyl.

Preferred are compounds wherein:

(a) protected hydroxy is selected from: dimethyl-t-butyl silyloxy, trimethylsilyloxy, tri-ethylsilyloxy, triisopropylsilyloxy, and triphenylsilyloxy;

(b) protected amino is acetylamino, benzoylamino, and pivaloylamino;

(c) C$_{1-10}$ alkyl is selected from methyl, ethyl, propyl, butyl, pentyl, 1,5-dimethylhexyl, 6-methylhept-2-yl, 5-methylhexyl, and 1-methyl-4-isopropylhexyl;

(d) substituted or unsubstituted C$_{2-10}$alkenyl is selected from: phenylmethylene, chlorophenylmethylene, ethoxycarbonylphenylmethylene, carboxyphenylmethylene, (((1,1-dimethylethyl)amino)carbonyl)phenylmethylene, trimethoxyphenyl methylene, methoxyphenylmethylene, methylsulfonylphenylmethylene, biphenylmethylene, nitrophenylmethylene, aminophenylmethylene, acetylaminophenylmethylene, pivaloylaminophenylmethylene, phenoxyphenylmethylene, 2-imidazolyl methylene, 2-thiazolylmethylene, (e) aryl substituted C$_{1-10}$ alkyl is selected from omega-phenylpropyl and 1-(chlorophenoxy)ethyl;

(f) aryl is selected from phenyl, and naphthyl;

(g) substituted aryl or heteroaryl is selected from phenyl, pyridyl and pyrimidinyl substituted with one to three substituents independently selected from:
(1) —H,
(2) —OH,
(3) —CH$_3$,
(4) —OCH$_3$,
(5) —S(O)$_n$—CH$_3$, wherein n is selected from 0, 1, and 2,
(6) —CF$_3$,
(7) halo,
(8) —CHO,
(9) CN,
(10) phenyloxy,
(11) ethyl,
(12) t-butyl,
(13) OCH$_2$CH$_3$,
(14) OC(CH$_3$)$_3$, and
(15) —NHR$^7$, wherein R$^7$ is selected from: —H, —C$_{1-8}$ alkyl, —C$_{1-6}$ alkylcarbonyl, —C$_{1-6}$ alkylsulfonyl, and —C$_{1-6}$ alkoxycarbonyl, (h) aryl or heteroaryl carbamoyl substituted C$_{1-10}$ alkyl is selected from 2-(4-pyridyl-carbamoyl)ethyl and 2-phenyl-ethyl;

(i) C$_{1-10}$alkylcarbonyl is selected from isobutylcarbonyl and isopropylcarbonyl;

(j) aryl or heteroaryl carbonyl is selected from phenylcarbonyl and pyridyl carbonyl;

(k) ether-substituted C$_{1-10}$alkyl is selected from 1-methoxy-ethyl and 1-ethoxy-ethyl;

(l) thioether-substituted C$_{1-10}$alkyl is selected from 1-methylthio-ethyl, and 1-ethylthio-ethyl;

(m) keto-substituted C$_{1-10}$alkyl is 1-keto-ethyl, ketomethyl, 1-ketopropyl, and ketobutyl;

(n) heteroaryl-substituted C$_{1-10}$ alkyl is omega-(4-pyridyl)butyl;

(o) carboxylic esters are C$_{1-10}$ alkylcarboxylic esters selected from carbomethoxy and carboethoxy;

(p) carboxamides are selected from N,N-diisopropyl carboxamide, N-t-butyl carboxamide, N-t-octyl carboxamide, N-n-octyl carboxamide, N-(hydroxyphenyl)carboxamide, N-phenylcarboxamide, N-(aminophenyl)carboxamide, N-(carbomethoxy)phenyl carboxamide, N-(methoxycarboxy)phenyl carboxamide, N-acetamidophenyl-N-acetyl-carboxamide, N-acetamidophenyl-carboxamide, N-pivalamidophenyl carboxamide, N-isobutyramidophenyl carboxamide, N-(methyl),N-diphenylmethyl)carboxamide, N-(diphenylmethyl)-carboxamide, N-t-butyl carboxamide, N-isopropyl carboxamide, 1-adamantyl carboxamide, 2-adamantyl carboxamide and N-(substituted phenyl)carboxamides wherein the phenyl may be substituted with 1 to 2 substitutents selected from ethyl, methyl, trifluoromethyl or halo (F, Cl, Br, I);

(q) C$_{1-10}$alkanoyloxyC$_{1-2}$alkyl is selected from acetyloxymethyl, trimethylacetyloxymethyl, and (2-ethylhexanoyloxy)methyl;

(r) urea is t-butylcarbonylamino urea;

(s) C$_{1-10}$ alkylureido C$_{0-5}$ alkyl is selected from: N-t-butylureidomethyl, N-n-propylureidomethyl, N-n-octylureidomethyl, N-isopropylureido, allylureido, (t) substituted or unsubstituted arylureidoC$_{0-5}$ alkyl is selected from: N-(ethylphenyl)ureidomethyl, N-(chlorophenyl)ureidomethyl, N-phenylureidomethyl, N-(dichlorophenyl)ureidomethyl, N-naphth-2-yl)ureidomethyl, N-thiazol-2-ylureidomethyl, N-thien-2-ylmethylureidomethyl, N-(fluorophenyl)ureido, N-(methoxyphenyl)ureido, and 2-(ethoxyphenyl)ureidomethyl;

(u) C$_{1-10}$ alkylcarbonylamino is t-butylcarbonylamino;

(v) alkanoylamidoalkyl is selected from: trimethylacetamidomethyl, carbomethoxyoctanoylamidomethyl, (isobutylphenyl)propionamidomethyl, 8-carboxyoctanoylamidomethyl, bromohexanoylamido methyl, hydroxydodecanoyl amidomethyl, 4-nitrophenylprionamidomethyl, isopropylthioacetamidomethyl, benzyloxyacetamidomethyl, carbomethoxyacetamidomethyl, triphenylproprionamidomethyl, cyclohexylacetamidomethyl, methylcyclohexanecarboxamidomethyl, (3-hydroxy-4,4,4-trichlorobutyramido)methyl, and phenylthioacetamidomethyl;

(w) ether is selected from ethylene ketal, and C$_{1-8}$alkyl ether optionally substituted with hydroxy, halo, C$_{1-8}$alkoxy, C$_{2-6}$alkenyl, or aryl;

(x) thioether is selected from: C$_{1-8}$alkylthio, phenylthio, and C$_{1-8}$ alkylthio substituted with phenyl; and (y) substituted and unsubstituted aryl or heteroaryl ether is selected from thiophenoxy, biphenyloxy, acetamidophenoxy, (3-pyridyl)oxy, chlorophenyloxy, methylphenyloxy, phenoxy, hydroxyphenyloxy, methylsulfonylphenyloxy and pyrimidinyloxy.

In one embodiment of the instant invention are compounds of formula I wherein X is oxygen.

In one class of the compounds of this embodiment are compounds wherein Z is

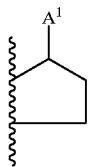

Exemplifying this class are:
(1) N-t-Butyl-4-oxa-5α-androst-1-en-3-one-17β-carboxamide,
(2) 7β-Methyl-4-oxa-5α-cholest-1-en-3-one,
(3) 17β-(2,5-bis(trifluoromethyl)phenylcarbamoyl)-4-oxa-5α-androst-1-en-3-one,
(4) 17β-(2,3-bis(trifluoromethyl)phenylcarbamoyl)-4-oxa-5α-androst-1-en-3-one,
(5) 17β-(2,4-bis(trifluoromethyl)phenylcarbamoyl)-4-oxa-5α-androst-1-en-3-one,
(6) 17β-(2,6-bis(trifluoromethyl)phenylcarbamoyl)-4-oxa-5α-androst-1-en-3-one,
(7) 17β-(N-tert-amylcarbamoyl)-4-oxa-5α-androst-1-en-3-one,
(8) 17β-(N-tert-hexylcarbamoyl)-4-oxa-5α-androst-1-en-3-one,
(9) 17β-(N-isobutylcarbamoyl)-4-oxa-5α-androst-1-en-3-one,
(10) 17β-(N-tert-octylcarbamoyl)-4-oxa-5α-androst-1-en-3-one,
(11) 17β-(N-1,1-diethylbutylcarbamoyl)-4-oxa-5α-androst-1-en-3-one,
(12) 17β-(N-neopentylcarbamoyl)-4-oxa-5α-androst-1-en-3-one,
(13) 17β-(N-2-adamantylcarbamoyl)-4-oxa-5α-androst-1-en-3-one,
(14) 17β-(N-1-adamantylcarbamoyl)-4-oxa-5α-androst-1-en-3-one,
(15) 17β-(N-2-norbornylcarbamoyl)-4-oxa-5α-androst-1-en-3-one,
(16) 17β-(N-1-norbornylcarbamoyl)-4-oxa-5α-androst-1-en-3-one,
(17) 17β-(N-phenylcarbamoyl)-4-oxa-5α-androst-1-en-3-one,
(18) 17β-(N-benzylcarbamoyl)-4-oxa-5α-androst-1-en-3-one,
(19) 17β-(2,3-bis(trifluoromethyl)phenylcarbamoyl)-7β-methyl-4-oxa-5α-androst-1-en-3-one,
(20) 17β-(2,4-bis(trifluoromethyl)phenylcarbamoyl)-7β-methyl-4-oxa-5α-androst-1-en-3-one,
(21) 17β-(2,6-bis(trifluoromethyl)phenylcarbamoyl)-7β-methyl-4-oxa-5α-androst-1-en-3-one,
(22) 17β-(N-n-octylcarbamoyl)-4-methyl-4-oxa-5α-androst-1-en-3-one,
(23) 17β-(1-methoxyethyl)-7β-methyl-4-oxa-5α-androst-1-en-3-one,
(24) 17β-(isopropyl)-7β-methyl-4-oxa-5α-androst-1-en-3-one,
(25) 17β-(4-methyl-phenoxy)-7β-methyl-4-oxa-5α-androst-1-en-3-one,
(26) 17β-(1-(3-chlorophenoxy)ethyl)-7β-methyl-4-oxa-5α-androst-1-en-3-one,
(27) 17β-(4-methylsulfonyl-phenoxy)-7β-methyl-4-oxa-5α-androst-1-en-3-one,
(28) 17β-(4-chlorophenoxy)-7β-methyl-4-oxa-5α-androst-1-en-3-one,
(29) 17β-(2-pyrimidinyloxy)-7β-methyl-4-oxa-5α-androst-1-en-3-one, and
(30) 17β-(2,5-bis(trifluoromethyl)phenylcarbamoyl)-7β-methyl-4-oxa-5α-androst-1-en-3-one.

Further exemplifying this class are:
(1) N-t-Butyl-4-oxa-5α-androst-1-en-3-one-17β-carboxamide,
(2) 7β-Methyl4-oxa-5α-cholest-1-en-3-one,
(3) 17β-(2,5-bis(trifluoromethyl)phenylcarbamoyl)-4-oxa-androst-1-en-3-one,
(4) 17β-(N-phenylcarbamoyl)-4-oxa-5α-androst-1-en-3-one,
(5) 17β-(N-benzylcarbamoyl)-4-oxa-5α-androst-1-en-3-one,
(6) 17β-(1-methoxyethyl)-7β-methyl-4-oxa-5α-androst-1-en-3-one,
(7) 17β-(isopropyl)-7β-methyl-4-oxa-5α-androst-1-en-3-one,
(8) 17β-(4-methylphenoxy)-7β-methyl-4-oxa-5α-androst-1-en-3-one,
(9) 17β-(1-(3-chlorophenyoxy)ethyl)-7β-methyl-4-oxa-5α-androst-1-en-3-one,
(10) 17β-(4-methylsulfonyl-phenoxy)-7β-methyl-4-oxa-5α-androst-1-en-3-one,
(11) 17β-(methyl-phenoxy)-7β-methyl-4-oxa-5α-androst-1-en-3-one,
(12) 17β-(4-chlorophenoxy)-7β-methyl-4-oxa-5α-androst-1-en-3-one,
(13) 17β-(2-pyrimidinyloxy)-7β-methyl-4-oxa-5α-androst-1-en-3-one, and
(14) 17β-(2,5-bis(trifluoromethyl)phenylcarbamoyl)-7β-methyl-4-oxa-5α-androst-1-en-3-one.

In one subclass of this class of the invention are compounds wherein $R^1$ is hydrogen, $R^2$ is selected from H and $CH_3$, and $A^1$ is selected from: carboxamide, including substituted and unsubstituted anilide derivatives.

Further illustrating this subclass are compounds wherein carboxamide is selected from: N,N-diisopropyl carboxamide, N-t-butyl carboxamide, N-t-octyl carboxamide, N-n-octyl carboxamide, N-(hydroxyphenyl) carboxamide, N-phenylcarboxamide, N-(aminophenyl) carboxamide, N-(carbomethoxy)phenyl carboxamide, N-(methoxycarboxy)phenyl carboxamide, N-acetamidophenyl-N-acetyl-carboxamide, N-acetamidophenyl-carboxamide, N-pivalamidophenyl carboxamide, N-isobutyramidophenyl carboxamide, N-(methyl),N-(diphenylmethyl)carboxamide, N-(diphenylmethyl)-carboxamide, N-t-butyl carboxamide, N-isopropyl carboxamide, 1-adamantyl carboxamide, 2-adamantyl carboxamide, and N-(substituted phenyl) carboxamides wherein the phenyl may be substituted with 1 to 2 substitutents selected from ethyl, methyl, trifluoromethyl or halo (F, Cl, Br, I).

Still further illustrating this subclass are compounds wherein carboxamide is —C(═O)NH—C(CH$_3$)$_3$, —C(═O)NH—C$_6$H$_5$ or —C(═O)NH-(2,5-trifluoromethylphenyl).

In one subclass of this class of the invention are compounds wherein R¹ is hydrogen, R² is selected from H and CH₃, the C5–C6 bond designated with a dotted line is a single bond, H$_a$ is present and represents hydrogen, and A¹ is selected from: carboxamide, including substituted and unsubstituted anilide derivatives.

Further illustrating this subclass are compounds wherein carboxamide is selected from: N,N-diisopropyl carboxamide, N-t-butyl carboxamide, N-t-octyl carboxamide, N-n-octyl carboxamide, N-(hydroxyphenyl) carboxamide, N-phenylcarboxamide, N-(aminophenyl) carboxamide, N-(carbomethoxy)phenyl carboxamide, N-(methoxycarboxy)phenyl carboxamide, N-acetamidophenyl-N-acetyl-carboxamide, N-acetamidophenyl-carboxamide, N-pivalamidophenyl carboxamide, N-isobutyramidophenyl carboxamide, N-(methyl),N-(diphenylmethyl)carboxamide, N-(diphenylmethyl)-carboxamide, N-t-butyl carboxamide, N-isopropyl carboxamide, 1-adamantyl carboxamide, 2-adamantyl carboxamide, and N-(substituted phenyl) carboxamides wherein the phenyl may be substituted with 1 to 2 substitutents selected from ethyl, methyl, trifluoromethyl or halo (F, Cl, Br, I).

Still further illustrating this subclass are compounds wherein carboxamide is —C(=O)NH—C(CH₃)₃, —C(=O)NH—C₆H₅ or —C(=O)NH-(2,5-trifluoromethylphenyl).

In one subclass of this class of the invention are compounds wherein R¹ is hydrogen, R² is selected from H and CH₃, the C5–C6 bond designated with a dotted line is a double bond, H$_a$ is absent, and A¹ is selected from: carboxamide, including substituted and unsubstituted anilide derivatives.

Further illustrating this subclass are compounds wherein carboxamide is selected from: N,N-diisopropyl carboxamide, N-t-butyl carboxamide, N-t-octyl carboxamide, N-n-octyl carboxamide, N-(hydroxyphenyl) carboxamide, N-phenylcarboxamide, N-(aminophenyl) carboxamide, N-(carbomethoxy)phenyl carboxamide, N-(methoxycarboxy)phenyl carboxamide, N-acetamidophenyl-N-acetyl-carboxamide, N-acetamidophenyl-carboxamide, N-pivalamidophenyl carboxamide, N-isobutyramidophenyl carboxamide, N-(methyl),N-(diphenylmethyl)carboxamide, N-(diphenylmethyl)-carboxamide, N-t-butyl carboxamide, N-isopropyl carboxamide, 1-adamantyl carboxamide, 2-adamantyl carboxamide and N-(substituted phenyl) carboxamides, wherein the phenyl may be substituted with 1 to 2 substitutents selected from ethyl, methyl, trifluoromethyl or halo (F, Cl, Br, I).

Still further illustrating this subclass are compounds wherein carboxamide is —C(=O)NH—C(CH₃)₃, —C(=O)NH—C₆H₅ or —C(=O)NH-(2,5-trifluoromethylphenyl).

In another subclass of this class of the invention are compounds wherein R¹ is CH₃, R² is selected from H and CH₃, and A¹ is a selected from: carboxamide, including substituted and unsubstituted anilide derivatives, and $C_{1-10}$ alkyl. Further illustrating this subclass are compounds wherein carboxamide is —C(=O)NH—C₆H₅ or —C(=O)NH-(2,5-trifluoromethylphenyl) and $C_{1-10}$ alkyl is selected from isopropyl, isobutyl, 1,5-dimethylhexyl, and 5-methylhexyl.

In another class of the compounds of this embodiment are compounds wherein Z is

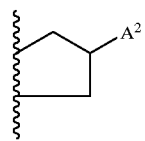

Exemplifying compounds of this class are:
(1) N-t-Butyl-4-oxa-5α-androst-1-en-3-one-16β-carboxamide,
(2) 16β-(1,5-dimethylhexyl)-7β-Methyl-4-oxa-5α-androst-1-en-3-one,
(3) 16β-(2,5-bis(trifluoromethyl)phenylcarbamoyl)-4-oxa-androst-1-en-3-one,
(4) 16β-(N-tert-amylcarbamoyl)-4-oxa-5α-androst-1-en-3-one,
(5) 16β-(N-tert-hexylcarbamoyl)-4-oxa-5α-androst-1-en-3-one,
(6) 16β-(N-isobutylcarbamoyl)-4-oxa-5α-androst-1-en-3-one,
(7) 16β-(N-tert-octylcarbamoyl)-4-oxa-5α-androst-1-en-3-one,
(8) 16β-(N-1,1-diethylbutylcarbamoyl)-4-oxa-5α-androst-1-en-3-one,
(9) 16β-(N-neopentylcarbamoyl)-4-oxa-5α-androst-1-en-3-one,
(10) 16β-(N-2-adamantylcarbamoyl)-4-oxa-5α-androst-1-en-3-one,
(11) 16β-(N-1-adamantylcarbamoyl)-4-oxa-5α-androst-1-en-3-one,
(12) 16β-(N-2-norbomylcarbamoyl)-4-oxa-5α-androst-1-en-3-one,
(13) 16β-(N-1-norbomylcarbamoyl)-4-oxa-5α-androst-1-en-3-one,
(14) 16β-(N-phenylcarbamoyl)-4-oxa-5α-androst-1-en-3-one,
(15) 16β-(N-benzylcarbamoyl)-4-oxa-5α-androst-1-en-3-one,
(16) 16β-(2,3-bis(trifluoromethyl)phenylcarbamoyl)-7β-methyl-4-oxa-5α-androst-1-en-3-one,
(17) 16β-(2,4-bis(trifluoromethyl)phenylcarbamoyl)-7β-methyl-4-oxa-5α-androst-1-en-3-one,
(18) 16β-(2,6-bis(trifluoromethyl)phenylcarbamoyl)-7β-methyl-4-oxa-5α-androst-1-en-3-one,
(19) 16β-(2,3-bis(trifluoromethyl)phenylcarbamoyl)-4-oxa-androst-1-en-3-one,
(20) 16β-(2,4-bis(trifluoromethyl)phenylcarbamoyl)-4-oxa-androst-1-en-3-one,
(21) 16β-(2,6-bis(trifluoromethyl)phenylcarbamoyl)-4-oxa-androst-1-en-3-one,
(22) 16β-(N-n-octylcarbamoyl)-4-methyl-4-oxa-5α-androst-1-en-3-one,
(23) 16β-(1-methoxyethyl)-7β-methyl-4-oxa-5α-androst-1-en-3-one,
(24) 16β-(isopropyl)-7β-methyl-4-oxa-5α-androst-1-en-3-one,
(25) 16β-(4-methyl-phenoxy)-7β-methyl-4-oxa-5α-androst-1-en-3-one,
(26) 16β-(1-(3-chlorophenoxy)ethyl)-7β-methyl-4-oxa-5α-androst-1-en-3-one,
(27) 16β-(4-methylsulfonyl-phenoxy)-7β-methyl-4-oxa-5α-androst-1-en-3-one,

(28) 16β-(4-chlorophenoxy)-7β-methyl-4-oxa-5α-androst-1-en-3-one,
(29) 16β-(2-pyrimidinyloxy)-7β-methyl-4-oxa-5α-androst-1-en-3-one, and
(30) 16β-(2,5-bis(trifluoromethyl)phenylcarbamoyl)-7β-methyl-4-oxa-5α-androst-1-en-3-one.

Further exemplifying the compounds of this class are:
16β-(4-methyl-phenoxy)-7β-methyl-4-oxa-5α-androst-1-en-3-one,
16β-(1-(3-chlorophenoxy)ethyl)-7β-methyl-4-oxa-5α-androst-1-en-3-one,
16β-(4-methylsulfonyl-phenoxy)-7β-methyl4-oxa-5α-androst-1-en-3-one,
16β-(4-chlorophenoxy)-7β-methyl-4-oxa-5α-androst-1-en-3-one, and
16β-(2-pyrimidinyloxy)-7β-methyl-4-oxa-5α-androst-1-en-3-one.

In one subclass of this class, $R^1$ is $C_{1-5}$ alkyl, $R^2$ is selected from hydrogen and methyl, and $A^2$ is selected from: alkoxy, aryloxy, either unsubstituted or substituted, heteroaryloxy, either substituted or unsubstituted, and alkyl, either unsubstituted or substituted.

Further illustrating this subclass are compounds wherein, $A^2$ is selected from: substituted aryloxy, and heteroaryloxy, either substituted or unsubstituted.

Exemplifying compounds of this subclass are compounds wherein the C5–C6 bond designated with a dotted line is a single bond, and $H_a$ is present and represents hydrogen.

Further exemplifying the compounds of this subclass are compounds wherein the C5–C6 bond designated with a dotted line is a double bond, and $H_a$ is absent.

In one subclass of this class, $R^1$ is H or $CH_3$, $R^2$ is selected from H and $CH_3$, and $A^2$ is selected from: substituted and unsubstituted aryl or heteroaryl ether. Further illustrating this subclass are the compounds wherein substituted and unsubstituted aryl or heteroaryl ether is selected from thiophenoxy, biphenyloxy, acetamidophenoxy, (3-pyridyl) oxy, chlorophenyloxy, methylphenyloxy, phenoxy, hydroxyphenyloxy, methylsulfonylphenyloxy and pyrimidinyloxy. Still further illustrating the compounds of the present invention are compounds wherein substituted or unsubstituted aryl or heteroaryl ether is selected from 4-methyl-phenoxy, 4-chlorophenoxy, and 2-pyrimidinyloxy.

In another embodiment of the instant invention are compounds of formula I wherein X is sulfur.

In one class of the compounds of this embodiment are compounds wherein Z is

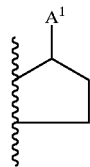

Exemplifying compounds of this class are:
(1) N-t-Butyl-4-thia-5α-androst-1-en-3-one-17β-carboxamide,
(2) 7β-Methyl-4-thia-5α-cholest-1-en-3-one,
(3) 17β-(2,5-bis(trifluoromethyl)phenylcarbamoyl)-4-thia-5α-androst-1-en-3-one,
(4) 17β-(2,3-bis(trifluoromethyl)phenylcarbamoyl)-4-thia-5α-androst-1-en-3-one,
(5) 17β-(2,4-bis(trifluoromethyl)phenylcarbamoyl)-4-thia-5α-androst-1-en-3-one,
(6) 17β-(2,6-bis(trifluoromethyl)phenylcarbamoyl)-4-thia-5α-androst-1-en-3-one,
(7) 17β-(N-tert-amylcarbamoyl)-4-thia-5α-androst-1-en-3-one,
(8) 17β-(N-tert-hexylcarbamoyl)-4-thia-5α-androst-1-en-3-one,
(9) 17β-(N-isobutylcarbamoyl)-4-thia-5α-androst-1-en-3-one,
(10) 17β-(N-tert-octylcarbamoyl)-4-thia-5α-androst-1-en-3-one,
(11) 17β-(N-1,1-diethylbutylcarbamoyl)-4-thia-5α-androst-1-en-3-one,
(12) 17β-(N-neopentylcarbamoyl)-4-thia-5α-androst-1-en-3-one,
(13) 17β-(N-2-adamantylcarbamoyl)-4-thia-5α-androst-1-en-3-one,
(14) 17β-(N-1-adamantylcarbamoyl)-4-thia-5α-androst-1-en-3-one,
(15) 17β-(N-2-norbornylcarbamoyl)-4-thia-5α-androst-1-en-3-one,
(16) 17β-(N-1-norbornylcarbamoyl)-4-thia-5α-androst-1-en-3-one,
(17) 17β-(N-phenylcarbamoyl)-4-thia-5α-androst-1-en-3-one,
(18) 17β-(N-benzylcarbamoyl)-4-thia-5α-androst-1-en-3-one,
(19) 17β-(2,3-bis(trifluoromethyl)phenylcarbamoyl)-7β-methyl-4-thia-5α-androst-1-en-3-one,
(20) 17β-(2,4-bis(trifluoromethyl)phenylcarbamoyl)-7β-methyl-4-thia-5α-androst-1-en-3-one,
(21) 17βp-(2,6-bis(trifluoromethyl)phenylcarbamoyl)-7β-methyl-4-thia-5α-androst-1-en-3-one,
(22) 17β-(N-n-octylcarbamoyl)-4-methyl-4-thia-5α-androst-1-en-3-one,
(23) 17β-(1-methoxyethyl)-7β-methyl-4-thia-5α-androst-1-en-3-one,
(24) 17β-(isopropyl)-7β-methyl-4-thia-5α-androst-1-en-3-one,
(25) 17β-(4-methyl-phenoxy)-7β-methyl-4-thia-5α-androst-1-en-3-one,
(26) 17β-(1-(3-chlorophenoxy)ethyl)-7β-methyl-4-thia-5α-androst-1-en-3-one,
(27) 17β-(4-methylsulfonyl-phenoxy)-7β-methyl-4-thia-5α-androst-1-en-3-one,
(28) 17β-(4-chlorophenoxy)-7β-methyl-4-thia-5α-androst-1-en-3-one,
(29) 17β-(2-pyrimidinyloxy)-7β-methyl-4-thia-5α-androst-1-en-3-one, and
(30) 17β-(2,5-bis(trifluoromethyl)phenylcarbamoyl)-7β-methyl-4-thia-5α-androst-1-en-3-one.

Further exemplifying compounds of this class are:
(1) N-t-Butyl-4-thia-5α-androst-1-en-3-one-17β-carboxamide,
(2) 7β-Methyl-4-thia-5α-cholest-1-en-3-one,
(3) 17β-(2,5-bis(trifluoromethyl)phenylcarbamoyl)-4-thia-androst-1-en-3-one,
(4) 17β-(N-phenylcarbamoyl)-4-thia-5α-androst-1-en-3-one,
(5) 17β-(N-benzylcarbamoyl)-4-thia-5α-androst-1-en-3-one,
(6) 17β-(1-methoxyethyl)-7β-methyl-4-thia-5α-androst-1-en-3-one, (7) 17β-(isopropyl)-7β-methyl-4-thia-5α-androst-1-en-3-one, (8) 17β-(4-methylphenoxy)-7β-methyl-4-thia-5α-androst-1-en-3-one, (9) 17β-(1-(3-chlorophenyoxy)ethyl)-7β-methyl-4-thia-5α-androst-1-en-3-one,

(10) 17β-(4-methylsulfonyl-phenoxy)-7β-methyl-4-thia-5α-androst-1-en-3-one,

(11) 17β-(methyl-phenoxy)-7β-methyl-4-thia-5α-androst-1-en-3-one,

(12) 17β-(4-chlorophenoxy)-7β-methyl-4-thia-5α-androst-1-en-3-one,

(13) 17β-(2-pyrimidinyloxy)-7β-methyl-4-thia-5α-androst-1-en-3-one, and

(14) 17β-(2,5-bis(trifluoromethyl)phenylcarbamoyl)-7β-methyl-4-thia-5α-androst-1-en-3-one.

In one subclass of this class of the invention are compounds wherein $R^1$ is hydrogen, $R^2$ is selected from H and $CH_3$, and $A^1$ is selected from: carboxamide, including substituted and unsubstituted anilide derivatives.

Further illustrating this subclass are compounds wherein carboxamide is selected from: N,N-diisopropyl carboxamide, N-t-butyl carboxamide, N-t-octyl carboxamide, N-n-octyl carboxamide, N-(hydroxyphenyl) carboxamide, N-phenylcarboxamide, N-(aminophenyl) carboxamide, N-(carbomethoxy)phenyl carboxamide, N-(methoxycarboxy)phenyl carboxamide, N-acetamidophenyl-N-acetyl-carboxamide, N-acetamidophenyl-carboxamide, N-pivalamidophenyl carboxamide, N-isobutyramidophenyl carboxamide, N-(methyl),N-(diphenylmethyl)carboxamide, N-(diphenylmethyl)-carboxamide, N-t-butyl carboxamide, N-isopropyl carboxamide, 1-adamantyl carboxamide, 2-adamantyl carboxamide, and N-(substituted phenyl) carboxamides wherein the phenyl may be substituted with 1 to 2 substitutents selected from ethyl, methyl, trifluoromethyl or halo (F, Cl, Br, I).

Still further illustrating this subclass are compounds wherein carboxamide is —C(=O)NH—C(CH$_3$)$_3$, —C(=O)NH—C$_6$H$_5$ or —C(=O)NH-(2,5-trifluoromethylphenyl).

In one subclass of this class of the invention are compounds wherein $R^1$ is hydrogen, $R^2$ is selected from H and $CH_3$, the C5–C6 bond designated with a dotted line is a single bond, $H_a$ is present and represents hydrogen, and $A^1$ is selected from: carboxamide, including substituted and unsubstituted anilide derivatives.

Further illustrating this subclass are compounds wherein carboxamide is selected from: N,N-diisopropyl carboxamide, N-t-butyl carboxamide, N-t-octyl carboxamide, N-n-octyl carboxamide, N-(hydroxyphenyl) carboxamide, N-phenylcarboxamide, N-(aminophenyl) carboxamide, N-(carbomethoxy)phenyl carboxamide, N-(methoxycarboxy)phenyl carboxamide, N-acetamidophenyl-N-acetyl-carboxamide, N-acetamidophenyl-carboxamide, N-pivalamidophenyl carboxamide, N-isobutyramidophenyl carboxamide, N-(methyl),N-diphenylmethyl)carboxamide, N-(diphenylmethyl)-carboxamide, N-t-butyl carboxamide, N-isopropyl carboxamide, 1-adamantyl carboxamide, 2-adamantyl carboxamide, and N-(substituted phenyl) carboxamides wherein the phenyl may be substituted with 1 to 2 substitutents selected from ethyl, methyl, trifluoromethyl or halo (F, Cl, Br, I).

Still further illustrating this subclass are compounds wherein carboxamide is —C(=O)NH—C(CH$_3$)$_3$, —C(=O)NH—C$_6$H$_5$ or —C(=O)NH-(2,5-trifluoromethylphenyl).

In one subclass of this class of the invention are compounds wherein $R^1$ is hydrogen, $R^2$ is selected from H and $CH_3$, the C5–C6 bond designated with a dotted line is a double bond, $H_a$ is absent, and $A^1$ is selected from: carboxamide, including substituted and unsubstituted anilide derivatives.

Further illustrating this subclass are compounds wherein carboxamide is selected from: N,N-diisopropyl carboxamide, N-t-butyl carboxamide, N-t-octyl carboxamide, N-n-octyl carboxamide, N-(hydroxyphenyl) carboxamide, N-phenylcarboxamide, N-(aminophenyl) carboxamide, N-(carbomethoxy)phenyl carboxamide, N-(methoxycarboxy)phenyl carboxamide, N-acetamidophenyl-N-acetyl-carboxamide, N-acetamidophenyl-carboxamide, N-pivalamidophenyl carboxamide, N-isobutyramidophenyl carboxamide, N-(methyl),N-(diphenylmethyl)carboxamide, N-(diphenylmethyl)-carboxamide, N-t-butyl carboxamide, N-isopropyl carboxamide, 1-adamantyl carboxamide, 2-adamantyl carboxamide and N-(substituted phenyl) carboxamides, wherein the phenyl may be substituted with 1 to 2 substitutents selected from ethyl, methyl, trifluoromethyl or halo (F, Cl, Br, I).

Still further illustrating this subclass are compounds wherein carboxamide is —C(=O)NH—C(CH$_3$)$_3$, —C(=O)NH—C$_6$H$_5$ or —C(=O)NH-(2,5-trifluoromethylphenyl).

In another subclass of this class of the invention are compounds wherein $R^1$ is $CH_3$, $R^2$ is selected from H and $CH_3$, and $A^1$ is a selected from: carboxamide, including substituted and unsubstituted anilide derivatives, and $C_{1-10}$ alkyl. Further illustrating this subclass are compounds wherein carboxamide is —C(=O)NH—C$_6$H$_5$ or —C(=O)NH-(2,5-trifluoromethylphenyl) and $C_{1-10}$ alkyl is selected from isopropyl, isobutyl, 1,5-dimethylhexyl, and 5-methylhexyl.

In another class of the compounds of this embodiment are compounds wherein Z is

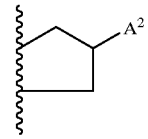

Exemplifying compounds of this class are:

(1) N-t-Butyl-4-thia-5α-androst-1-en-3-one-16β-carboxamide, (2) 16β-(1,5-dimethylhexyl)-7β-Methyl-4-thia-5α-androst-1-en-3-one, (3) 16β-(2,5-bis(trifluoromethyl)phenylcarbamoyl)-4-thia-androst-1-en-3-one, (4) 16β-(N-tert-amylcarbamoyl)-4-thia-5α-androst-1-en-3-one, (5) 16β-(N-tert-hexylcarbamoyl)-4-thia-5α-androst-1-en-3-one, (6) 16β-(N-isobutylcarbamoyl)-4-thia-5α-androst-1-en-3-one, (7) 16β-(N-tert-octylcarbamoyl)-4-thia-5α-androst-1-en-3-one, (8) 16β-(N-1,1-diethylbutylcarbamoyl)-4-thia-5α-androst-1-en-3-one, (9) 16β-(N-neopentylcarbamoyl)-4-thia-5α-androst-1-en-3-one,

(10) 16β-(N-2-adamantylcarbamoyl)-4-thia-5α-androst-1-en-3-one,

(11) 16β-(N-1-adamantylcarbamoyl)-4-thia-5α-androst-1-en-3-one,

(12) 16β-(N-2-norbornylcarbamoyl)-4-thia-5α-androst-1-en-3-one,

(13) 16β-(N-1-norbornylcarbamoyl)-4-thia-5α-androst-1-en-3-one,

(14) 16β-(N-phenylcarbamoyl)-4-thia-5α-androst-1-en-3-one,

(15) 16β-(N-benzylcarbamoyl)-4-thia-5α-androst-1-en-3-one,

(16) 16β-(2,3-bis(trifluoromethyl)phenylcarbamoyl)-7β-methyl-4-thia-5α-androst-1-en-3-one,

(17) 16β-(2,4-bis(trifluoromethyl)phenylcarbamoyl)-7β-methyl-4-thia-5α-androst-1-en-3-one,

(18) 16β-(2,6-bis(trifluoromethyl)phenylcarbamoyl)-7β-methyl-4-thia-5α-androst-1-en-3-one,

(19) 16β-(2,3-bis(trifluoromethyl)phenylcarbamoyl)-4-thia-androst-1-en-3-one,

(20) 16β-(2,4-bis(trifluoromethyl)phenylcarbamoyl)-4-thia-androst-1-en-3-one,

(21) 16β-(2,6-bis(trifluoromethyl)phenylcarbamoyl)-4-thia-androst-1-en-3-one,

(22) 16β-(N-n-octylcarbamoyl)-4-methyl-4-thia-5α-androst-1-en-3-one,

(23) 16β-(1-methoxyethyl)-7β-methyl-4-thia-5α-androst-1-en-3-one,

(24) 16β-(isopropyl)-7β-methyl-4-thia-5α-androst-1-en-3-one,

(25) 16β-(4-methyl-phenoxy)-7β-methyl-4-thia-5α-androst-1-en-3-one,

(26) 16β-(1-(3-chlorophenoxy)ethyl)-7β-methyl-4-thia-5α-androst-1-en-3-one,

(27) 16β-(4-methylsulfonyl-phenoxy)-7β-methyl-4-thia-5α-androst-1-en-3-one,

(28) 16β-(4-chlorophenoxy)-7β-methyl-4-thia-5α-androst-1-en-3-one,

(29) 16β-(2-pyrimidinyloxy)-7β-methyl-4-thia-5α-androst-1-en-3-one, and

(30) 16β-(2,5-bis(trifluoromethyl)phenylcarbamoyl)-7β-methyl-4-thia-5α-androst-1-en-3-one.

Further exemplifying the compounds of this class are:

16β-(4-methyl-phenoxy)-7β-methyl-4-thia-5α-androst-1-en-3-one,

16β-(1-(3-chlorophenoxy)ethyl)-7β-methyl-4-thia-5α-androst-1-en-3-one,

16β-(4-methylsulfonyl-phenoxy)-7β-methyl-4-thia-5α-androst-1-en-3-one,

16β-(4-chlorophenoxy)-7β-methyl-4-thia-5α-androst-1-en-3-one, and

16β-(2-pyrimidinyloxy)-7β-methyl-4-thia-5α-androst-1-en-3-one.

In one subclass of this class, $R^1$ is $C_{1-5}$ alkyl, $R^2$ is selected from hydrogen and methyl, and $A^2$ is selected from: alkoxy, aryloxy, either unsubstituted or substituted, heteroaryloxy, either substituted or unsubstituted, and alkyl, either unsubstituted or substituted.

Further illustrating this subclass are compounds wherein, $A^2$ is selected from: substituted aryloxy, and heteroaryloxy, either substituted or unsubstituted.

Exemplifying compounds of this subclass are compounds wherein the C5–C6 bond designated with a dotted line is a single bond, and $H_a$ is present and represents hydrogen.

Further exemplifying the compounds of this subclass are compounds wherein the C5–C6 bond designated with a dotted line is a double bond, and $H_a$ is absent.

In another subclass of this class, $R^1$ is H or $CH_3$, $R^2$ is selected from H and $CH_3$, and $A^2$ is selected from: substituted and unsubstituted aryl or heteroaryl ether. Further illustrating this subclass are the compounds wherein substituted and unsubstituted aryl or heteroaryl ether is selected from thiophenoxy, biphenyloxy, acetamidophenoxy, (3-pyridyl)oxy, chlorophenyloxy, methylphenyloxy, phenoxy, hydroxyphenyloxy, methylsulfonylphenyloxy and pyrimidinyloxy. Still further illustrating the compounds of the present invention are compounds wherein substituted or unsubstituted aryl or heteroaryl ether is selected from 4-methyl-phenoxy, 4-chlorophenoxy, and 2-pyrimidinyloxy.

In one subclass of this class, $R^1$ is $C_{1-5}$ alkyl, $R^2$ is selected from hydrogen and methyl, and $A^2$ is selected from: alkoxy, aryloxy, either unsubstituted or substituted, heteroaryloxy, either substituted or unsubstituted, and alkyl, either unsubstituted or substituted.

Further illustrating this subclass are compounds wherein, $A^2$ is selected from: substituted aryloxy, and heteroaryloxy, either substituted or unsubstituted.

Exemplifying compounds of this subclass are compounds wherein the C5–C6 bond designated with a dotted line is a single bond, and $H_a$ is present and represents hydrogen.

Further exemplifying the compounds of this subclass are compounds wherein the C5–C6 bond designated with a dotted line is a double bond, and $H_a$ is absent.

When any variable (e.g., aryl, heterocycle, $R^1$, etc.) occurs more than one time in any constituent or in formula I, its definition on each occurrence is independent of its definition at every other occurrence. Also, combinations of substituents and/or variables are permissible only if such combinations result in stable compounds.

As used herein "alkyl" is intended to include both branched- and straight-chain saturated aliphatic hydrocarbon groups having the specified number of carbon atoms, e.g., methyl (Me), ethyl (Et), propyl, butyl, pentyl, hexyl, heptyl, octyl, nonanyl, decyl, undecyl, dodecyl, and the isomers thereof such as isopropyl (i-Pr), isobutyl (i-Bu), secbutyl (s-Bu), tertbutyl (t-Bu), isopentane, isohexane, etc. "Alkyloxy" (or "alkoxy") represents an alkyl group having the indicated number of carbon atoms attached through an oxygen bridge, e.g., methoxy, ethoxy, propyloxy, isopropoxy, n-butoxy, iso-butoxy, sec-butoxy, t-butoxy and the like.

The term "aryl" includes phenyl and naphthyl. Preferably, aryl is phenyl.

Heteroaryl is selected from piperidinyl, piperizinyl, pyrrolidinyl, pyrrolyl, furanyl, thienyl, pyridyl, pyrimidinyl, indolyl and benzofuranyl.

Heterocyclic rings may be attached to structural formula I at any heteroatom (N, O or S) or carbon atom in the ring which results in the creation of a stable, uncharged structure.

Hydroxy and amino protecting groups are known to those of ordinary skill in the art, and any such groups may be used. For example, acetate, benzoate, ether and silyl protecting groups are suitable hydroxy protecting groups. Standard silyl protecting groups have the general formula —Si(Xa)$_3$, wherein each Xa group is independently an alkyl or aryl group, and include, e.g. trimethylsilyl, tri-ethylsilyl, tri-i-propylsilyl, triphenylsilyl as well as t-butyl-di-(Xb)-silyl where Xb is methyl, ethyl, i-propyl or phenyl (Ph). Standard amino protecting groups have the general formula —C(O)—Xc, wherein Xc is alkyl, aryl, O-alkyl or O-aryl, and include, e.g. N-t-butoxycarbonyl. See also *Protective Groups in*

*Organic Synthesis*, T. W. Green et al. (John Wiley and Sons, 1991) for descriptions of protecting groups.

The compounds of the present invention may be administered in the form of pharmaceutically acceptable salts. The term "pharmaceutically acceptable salt" is intended to include all acceptable salts such as acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, panoate, valerate, and the like which can be used as a dosage form for modifying the solubility or hydrolysis characteristics or can be used in sustained release or pro-drug formulations. Depending on the particular functionality of the compound of the present invention, pharmaceutically acceptable salts of the compounds of this invention include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris (hydroxymethyl)aminomethane, and tetramethylammonium hydroxide. These salts may be prepared by standard procedures, e.g. by reacting a free acid with a suitable organic or inorganic base.

Also, in the case of an acid (—COOH) or alcohol group being present, pharmaceutically acceptable esters can be employed, e.g. methyl, ethyl, butyl, acetate, maleate, pivaloyloxymethyl, and the like, and those esters known in the art for modifying solubility or hydrolysis characteristics for use as sustained release or prodrug formulations.

The compounds of the present invention may have chiral centers other than those centers whose stereochemistry is depicted in formula I, and therefore may occur as racemates, racemic mixtures and as individual enantiomers or diastereomers, with all such isomeric forms being included in the present invention as well as mixtures thereof. Furthermore, some of the crystalline forms for compounds of the present invention may exist as polymorphs and as such are intended to be included in the present invention. In addition, some of the compounds of the instant invention may form solvates with water or common organic solvents. Such solvates are encompassed within the scope of this invention.

The term "therapeutically effective amount" is that amount of a drug or pharmaceutical agent that will elicit the biological or medical response of a tissue, system, animal or human that is being sought by a researcher, veterinarian, medical doctor or other clinician, which includes alleviation of the symptoms of the disorder being treated.

More particularly, the present invention relates to a method for treating hyperandrogenic conditions in a mammal in need of such treatment comprising the administration to the mammal in need of such treatment of a therapeutically effective amount of a compound of the present invention. The novel methods of treatment of this invention are for disorders known to those skilled in the art. The term "mammal" includes humans. Preferably, the method of the present invention is for treating hyperandrogenic conditions in a human in need of such treatment.

Hyperandrogenic conditions treatable by the method of the present invention include benign prostatic hyperplasia, androgenic alopecia (including male pattern baldness, female pattern baldness and female hirsutism), acne vulgaris, seborrhea, prostatitis and prostatic carcinoma.

The present invention has the objective of providing methods of treating hyperandrogenic conditions including androgenic alopecia, male pattern baldness, acne vulgaris, seborrhea, and female hirsutism by oral, systemic, parenteral or topical administration of the novel compounds of formula I either alone or in combination with a 5α-reductase 2 inhibitor, preferably selected from finasteride and epristeride, or a potassium channel opener, or a retinoic acid or derivative thereof. Alternatively, treatment may encompass administration of a combination of a compound of formula I with a 5α-reductase 2 inhibitor, preferably selected from finasteride and epristeride and another active agent such as a potassium channel opener, or a retinoic acid or derivative thereof. The term "treating androgenic alopecia" is intended to include the arresting and/or reversing of androgenic alopecia, and the promotion of hair growth.

The present invention has the further objective of providing methods of treating benign prostatic hyperplasia, prostatitis, and treating and/or preventing prostatic carcinoma by oral, systemic or parenteral administration of the novel compounds of formula I either alone or in combination with a 5α-reductase 2 inhibitor, preferably selected from finasteride and epristeride. Alternatively, treatment may encompass administration of a combination of a compound of formula I with a 5α-reductase 2 inhibitor and/or another active agent such as an α1 or an α1$_a$ adrenergic receptor antagonist (α1$_a$ receptor antagonists were formerly called α1$_c$ receptor antagonists).

The present invention also has a further objective of providing methods of treating acne vulgaris, androgenic alopecia, seborrhea, female hirsutism, benign prostatic hyperplasia, prostatitis and the preventing and/or treating of prostatic cancer, by oral, systemic, parental or topical administration of a combined therapy of a therapeutically effective amount of a compound of formula I with a therapeutically effective amount of an anti-androgen, such as, e.g., flutamide, spironolactone or casodex.

For combination treatment with more than one active agent, where the active agents are in separate dosage formulations, the active agents can be administered concomitantly, or they each can be administered at separately staggered times.

The present invention also has the objective of providing suitable topical, oral, systemic and parenteral pharmaceutical formulations for use in the novel methods of treatment of the present invention. The compositions containing the present compounds as the active ingredient for use in the treatment of the above-noted conditions can be administered in a wide variety of therapeutic dosage forms in conventional vehicles for systemic administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts.

An effective but non-toxic amount of the compound desired can be employed as an antiandrogenic agent.

The compounds of structural formula I useful in the present invention are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices may be administered systemically, by oral administration or by intravenous or intramuscular injection or topically.

For instance, for oral administration in the form of a tablet or capsule, the active drug component can be combined with an oral, non-toxic pharmaceutically acceptable inert carrier such as ethanol, glycerol, water and the like. Capsules containing the product of this invention can be prepared by mixing an active compound of the present invention with lactose and magnesium stearate, calcium stearate, starch, talc, or other carriers, and placing the mixture in gelatin capsules.

Tablets may be prepared by mixing the active ingredient with conventional tableting ingredients such as calcium phosphate, lactose, corn starch or magnesium stearate. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. Other dispersing agents which may be employed include glycerin and the like. For parenteral administration, sterile suspensions and solutions are desired. Isotonic preparations which generally contain suitable preservatives are employed when intravenous administration is desired.

Topical pharmaceutical compositions may be, e.g., in the form of a solution, cream, ointment, gel, lotion, shampoo or aerosol formulation adapted for application to the skin. Topical pharmaceutical compositions useful in the method of treatment of the present invention may include about 0.001% to 0.1% of the active compound in admixture with a pharmaceutically acceptable carrier.

Topical preparations containing the active drug component can be admixed with a variety of carrier materials well known in the art, such as, e.g., alcohols, aloe vera gel, allantoin, glycerine, vitamin A and E oils, mineral oil, propylene glycol, PPG2 myristyl propionate, and the like, to form, e.g., alcoholic solutions, topical cleansers, cleansing creams, skin gels, skin lotions, and shampoos in cream or gel formulations. See, e.g., EP 0 285 382.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxyethylaspartamide-phenol, or polyethyleneoxidepolylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

The compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter, arrest or reverse the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug. Preferably, doses of the compound of structural formula I useful in the method of the present invention range from 0.01 to 1000 mg per adult human per day. Most preferably, dosages range from 0.1 to 50 mg/day. For oral administration, the compositions are preferably provided in the form of tablets containing 0.01 to 1000 milligrams of the active ingredient, particularly 0.01, 0.05, 0.1, 0.5, 1.0, 2.5, 5.0, 10.0, 15.0, 25.0, and 50.0 milligrams of the active ingredient for the symptomatic adjustment of the dosage to the patient to be treated. An effective amount of the drug is ordinarily supplied at a dosage level of from about 0.0002 mg/kg to about 50 mg/kg of body weight per day. The range is more particularly from about 0.001 mg/kg to 1 mg/kg of body weight per day.

Advantageously, the active agent of the present invention may be administered in a single daily dose, or the total daily dosage may be administered in dividend doses of two, three or four times daily.

The compounds of the present invention may be used in the preparation of a medicament useful for the treatment of hyperandrogenic disorders including: acne vulgaris, androgenic alopecia, male pattern baldness, seborrhea, female hirsutism, benign prostatic hyperplasia, prostatitis and prostatic cancer.

For the treatment of acne vulgaris, androgenic alopecia, male pattern baldness, seborrhea, female hirsutism, benign prostatic hyperplasia, prostatitis and the prevention and/or treatment of prostatic cancer, the compounds of the instant invention can be combined with a therapeutically effective amount of another 5α-reductase inhibitor, such as finasteride or epristeride, or other 5α-reductase inhibitor compounds having type 2 activity, type 1 activity or dual activity for both isozymes, in a single oral, systemic, or parenteral pharmaceutical dosage formulation. Alternatively, a combined therapy can be employed wherein the compound of formula I and the other 5α-reductase inhibitor are administered in separate oral, systemic, or parenteral dosage formulations. Also, for the skin and scalp related disorders of acne vulgaris, androgenic alopecia, male pattern baldness, seborrhea, and female hirsutism, the compounds of the instant invention and another 5α-reductase inhibitor such as finasteride or epristeride can be formulated for topical administration. For example, a compound of formula I and finasteride can be administered in a single oral or topical dosage formulation, or each active agent can be administered in a separate dosage formulation, e.g., in separate oral dosage formulations, or an oral dosage formulation of finasteride in combination with a topical dosage formulation of a compound of formula I. See, e.g., U.S. Pat. Nos. 4,377,584 and 4,760,071 which describe dosages and formulations for 5α-reductase inhibitors.

Furthermore, administration of a compound of the present invention in combination with a therapeutically effective amount of a potassium channel opener, such as minoxidil, cromakalin, pinacidil, a compound selected from the classes of S-triazine, thiane-1-oxide, benzopyran, and pyridinopyran derivatives or a pharmaceutically acceptable salt thereof, may be used for the treatment of androgenic alopecia including male pattern baldness. Therapy may further comprise the administration of a 5α-reductase type 2 inhibitor such as finasteride or epristeride, or a 5α-reductase type 1 inhibitor, or a type 1 and type 2 dual inhibitor, in combination with a compound of the present invention and a potassium channel opener such as minoxidil. The active agents can be administered in a single topical dosage formulation, or each active agent can be administered in a separate dosage formulation, e.g., in separate topical dosage formulations, or an oral dosage formulation of a compound of formula I in combination with a topical dosage formulation of, e.g., minoxidil, or a single oral dosage formulation of a compound of formula I and another 5α-reductase inhibitor, in combination with a topical dosage formulation of, e.g., minoxidil. See, e.g., U.S. Pat. Nos. 4,596,812, 4,139,619 and WO 92/02225, published Feb. 20, 1992, for dosages and formulations of calcium channel openers.

Furthermore, for the treatment of acne vulgaris, a combined therapy can be used by administering a therapeutically effective amount of a compound of formula I in combination with a therapeutically effective amount of retinoic acid or a derivative thereof, e.g. an ester or amide derivative thereof, such as e.g., tretinoin or isotretinoin. Optionally, this combined therapy for acne vulgaris may further include a 5α-reductase type 2 inhibitor such as finasteride or epristeride, or a 5α-reductase type 1 inhibitor, or a dual type 1 and type 2 inhibitory compound.

Also, for the treatment of benign prostatic hyperplasia, a combined therapy comprising a administration of a compound of formula I with a 5α-reductase type 2 inhibitor, such as e.g., finasteride, and an alpha-1 adrenergic receptor antagonist, such as e.g., terazosin, doxazosin, prazosin, bunazosin, indoramin or alfuzosin, may be employed. More particularly, the combined therapy can comprise administering a compound of formula I with a 5α-reductase type 2 inhibitor, such as e.g., finasteride, and an alpha-1$_a$ adrenergic receptor antagonist (formerly called an alpha-1$_c$ adrenergic receptor antagonist). Compounds which are useful as alpha-1$_a$ adrenergic receptor antagonists can be identified according to procedures known to those of ordinary skill in the art, for example, as described in PCT/US93/09187 (WO94/08040, published Apr. 14, 1994); PCT/US94/03852 (WO 94/22829, published Oct. 13, 1994); PCT/US94/10162 (WO 95/07075, published Mar. 16, 1995), and U.S. Pat. No. 5,403,847.

Also, for the treatment of acne vulgaris, androgenic alopecia, seborrhea, female hirsutism, benign prostatic hyperplasia, prostatitis and the prevention and/or treatment of prostatic cancer, a combined therapy can be used by administering a therapeutically effective amount of a compound of formula I with a therapeutically effective amount of an anti-androgen, such as, e.g., flutamide, spironolactone or casodex.

For combination treatment with more than one active agent, where the active agents are in separate dosage formulations, the active agents can be administered concurrently, or they each can be administered at separately staggered times.

The compounds of the present invention can be prepared readily according to the following Schemes and Examples or modifications thereof using readily available starting materials, reagents and conventional synthesis procedures. In these reactions, it is also possible to make use of variants which are themselves known to those of ordinary skill in this art, but are not mentioned in greater detail.

The 4-oxa compounds of this invention can be prepared as shown in Scheme 1.

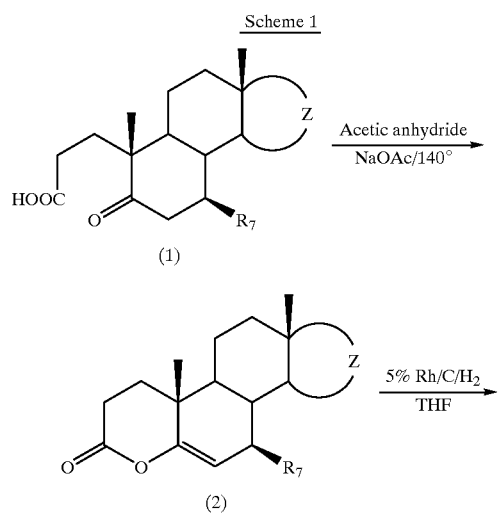

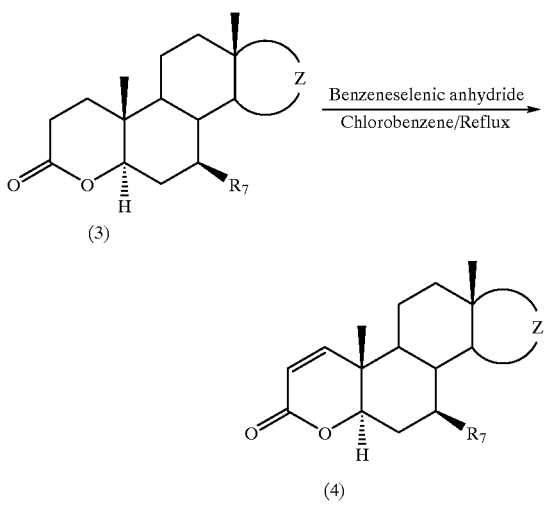

Scheme 1 outlines the synthesis of the novel oxasteroids of the present invention. The appropriately substituted seco-acid may be prepared by methods known in the art. PCT publication WO 95/11254 describes procedures for the synthesis of compounds having various substituents at the 16-position of the azasteroid. Starting with a 3-keto-delta4-17-one precursor and following the procedures of WO 95/11254, the appropriate $A^2$ substitution may be obtained. To obtain the appropriate $A^1$ substitution, the procedures of the following publications are followed starting with a 3-keto-delta4-17-one precursor: for ether or thioether WO 93/23040; for anilide WO 94/07861, EP 0 663 924; for unsubstituted, monosubstituted or disubstituted amides WO 93/23038, WO 93/23051, WO 93/23420; and U.S. Pat. Nos. 4,220,775, 4,760,071, 4,845,104, 5,237,067, 5,091,380, 5,061,801, 5,215,894, for oxo U.S. Pat. Nos. 4,220,775, 4,377,584; for cyano U.S. Pat. No. 4,220,775; for tetrazoyl U.S. Pat. No. 4,220,775; for arylalkylcarbonlyoxy alkyl U.S. Pat. No. 4,377,584; for cycloalkylarylcarbonlyoxy alkyl U.S. Pat. No. 4,377,584; for benzoyloxyalkyl U.S. Pat. No. 4,377,584; for acyl, both substituted and unsubstituted, U.S. Pat. No. 5,049,562, U.S. Pat. No. 5,138,063, U.S. Pat. No. 5,151,429, U.S. Pat. No. 5,237,061, U.S. Pat. No. 5,120,742, U.S. Pat. No. 5,162,332, U.S. Pat. No. 5,061,802, U.S. Pat. No. 5,098,908, U.S. Pat. No. 5,196,411, U.S. Pat. No. 5,075,450, U.S. Pat. No. 5,061,803, U.S. Pat. No. 5,324,734; for thiobenzyl U.S. Pat. No. 5,151,430; for polyaroyl U.S. Pat. No. 5,162,322; for ester U.S. Pat. No. 5,091,534, WO 93/23041, WO 93/23040, for alkyl, either substituted or unsubstituted WO 93/23050, WO 93/23419, WO 93/23051; for urea, thiourea, carbamate or thiocarbamate WO93/23048; for thioester WO 93/23041, WO 93/23040.

The appropriately 7,10,16, and 17-substituted 3-keto steroid is converted to the appropriately substituted seco-acid by methods known in the art, for example, the procedures described in Rasmusson, et al., J.Med.Chem. 1986, 29(11): 2298–2315.

The appropriate 7-β substitution may be obtained following the procedures for formation of a 7-β bond as described in U.S. Pat. Nos. 4,220,775, and 5,237,064.

Compounds wherein $R^2$ is H or $CH_2OR^3$ may be prepared starting with the appropriately C10 substituted seco-acid. These compounds may be made by procedures known in the art.

As shown in Scheme 1, the seco-acid (1) is treated with a dehydrating agent such as acetic anhydride, methyl ortho-formate, ethyl ortho-formate, in a nonpolar aprotic solvent such as toluene, xylene, dichloroethane, chlorobenzene and the like optionally in the presence of an acidic catalyst, such as PTSA (paratoluenesulfonic acid), or sodium acetate to form the $\Delta^5$-oxasteroid (2). Preferably, the seco-acid (1) is treated with acetic anhydride in acetic anhydride in the presence of sodium acetate at an elevated temperature, preferably at about 140° C. Hydrogenation of the double bond to form the oxasteroid (3) may be carried out in the presence of an appropriate catalyst such as Rh/C, Pd/C, etc., preferably Rh/C in a solvent such as tetrahydrofuran (THF) or ethyl acetate. This is followed by formation of the $\Delta^1$ double bond by treatment with, for example, dichlorodicyanoquinone (DDQ), benzeneselenic anhydride in chlorobenzene, or other known methods, for example as described in U.S. Pat. Nos. 5,084,574 and 5,021,571, to form the $\Delta^1$-oxasteroid (4).

The 4-thia compounds of this invention can be prepared as shown in Scheme 2.

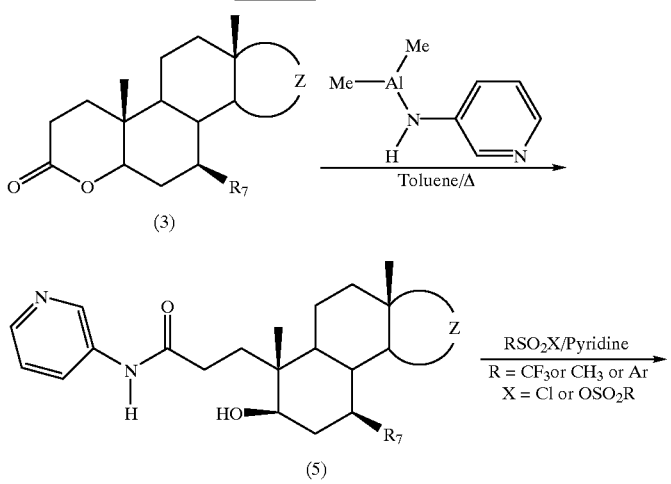

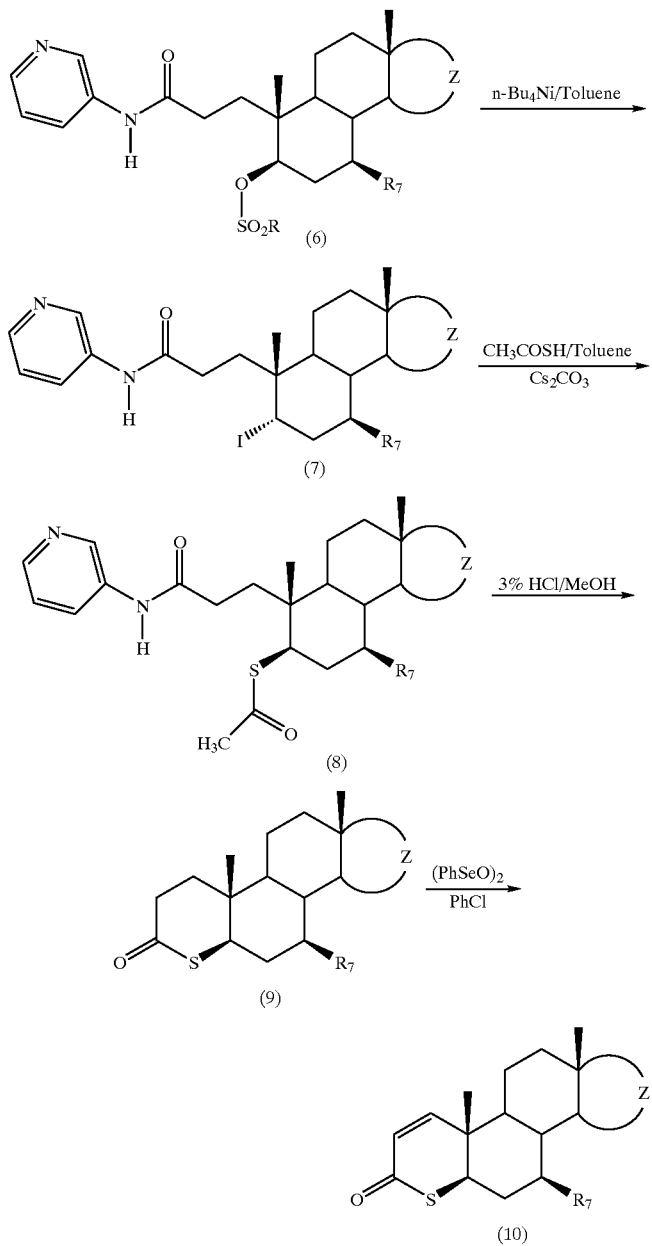

Starting with the 4-oxa-androstan-3-one appropriately substituted in the B and D-ring, obtained by following the procedures of Scheme 1 to obtain compound (3), the lactone is opened to form the hydroxamide (5). The lactone may be opened by various means such as treatment with dimethylalumino-3-aminopyridine (which may be prepared in situ by treating trimethyl aluminum with 3-amino pyridine), chlorobenzene or dichloroethane in a nonpolar, aprotic solvent such as toluene.

The hydroxamide (5) is treated with alkyl- or aryl sulfonyl chloride in a solvent such as methylene chloride, toluene or dichloroethane in the presence of a base such as pyridine, dimethylaminopyridine (DMAP), or N-methylpyrolidine (NMP), to give the corresponding alkyl- or aryl sulfonate (6). The reaction of the alkyl- or aryl sulfonate with tetrabutylammonium iodide in a polar aprotic solvent such as toluene produces the corresponding iodide (7). The iodide is treated with thioacetic acid in a nonpolar solvent such as toluene or dichloroethane in the presence of cesium carbonate or other base such as potassium carbonate or sodium carbonate to give the thioacetate (8). The thioacetate (8) is hydrolyzed to form the thialactone (9), preferably by treatment with acid in a polar solvent such as methanol or ethanol, preferably by treatment with hydrochloric acid in methanol. The thialactone (9) may be dehydrogenated to form the $\Delta^1$-thiasteroid (10) as described above, preferably by treatment with benzeneselenic anhydride in chlorobenzene at reflux.

The 4-oxa and 4-thia steroids of the present invention include the 1,2-5,6 diene which may be prepared by treating the compound of structural formula (2) with benzeneselenic anhydride in chlorobenzene with refluxing to obtain the $\Delta^1,\Delta^5$-oxasteroid derivative. The corresponding thiasteroid derivative may be obtained by following the procedures of Scheme 2, starting with (2), the $\Delta^5$-oxasteroid.

The following examples are not intended to be limitations on the scope of the instant invention in any way, and they should not be so construed. Furthermore, the compounds described in the following examples are not to be construed as forming the only genus that is considered as the invention, and any combination of the compounds or their moieties may itself form a genus. Those skilled in the art will readily understand that known variations of the conditions and processes of the following preparative procedures can be used to prepare these compounds.

All temperatures given in the following examples are in degrees Celsius. $^1H$ and $^{13}C$ nuclear magnetic resonance (NMR) spectra were taken at 400 or 500 MHz at ambient temperature in the solvents indicated. Some abbreviations used herein are as follows: "BOC" is t-butoxycarbonyl; "BOC anhydride" is di-t-butyl dicarbonate $\{O(CO_2C(CH_3)_3)_2\}$; "DBU" is 1,8-diaza-bicyclo[5.4,0]undec-7-ene; "DCC" is 1,3-dicyclohexylcarbodiimide; "DMS" is methyl sulfide $\{(CH_3)_2S\}$; "DMF" is dimethylformamide; "EtOAc" is ethyl acetate; "HOBT" is 1-hydroxybenzotriazole; "IPA" is isopropyl acetate; "Ph" is phenyl; "Tf" is $-SO_2CF_3$; "TFA" is trifluoroacetic acid; "THF" is tetrahydrofuran; "TIPS" is triisopropylsilyl; "TIPSO" is triisopropylsilyloxy. Unless otherwise specified "tlc" and "TLC" refer to thin layer $SiO_2$ chromatography.

EXAMPLE 1

Preparation of N-t-Butyl-4-oxa-5α-androst-1-en-3-one-17β-carboxamide

Step 1: Benzotriazol-1'-yl-3-oxo-androst-4-ene-17β-carboxamide

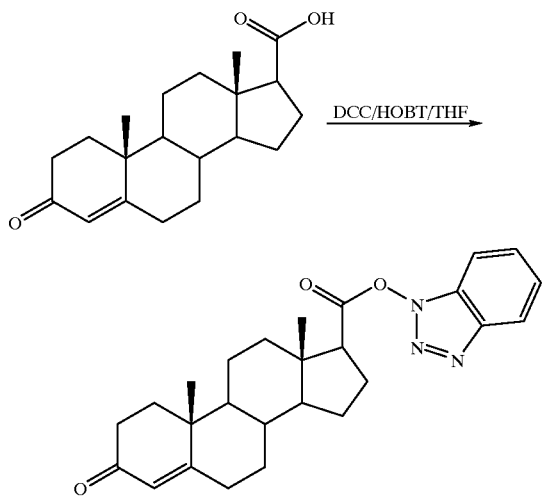

To a solution of steroid acid (4 g, 12.65 mmol, see Rasmusson et al., J.Med.Chem. 1986, 29(11): 2298–2315 for description of synthesis) in methylene chloride was added DCC (2.75 g, 13.3 mmol) and 1-hydroxybenzotriazole (HOBT, 2.75 g, 19.1 mmol). After stirring the reaction mixture for overnight, the solid was filtered, dried and used as such for further reactions.

Step 2: N-t-Butyl-3-oxo-androst-4-ene-17β-carboxamide

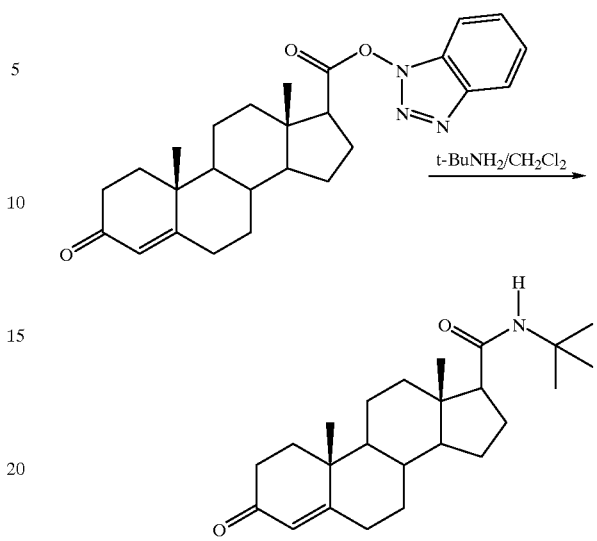

To a solution of benzotriazol-1'-yl-3-oxo-androst-4-ene-17β-carboxamide (1.5 g, 3.46 mmol) in methylene chloride was added t-butyl amine (454 μl, 4.33 mmol). After stirring the reaction mixture for overnight, the reaction mixture was concentrated, purified by chromatography over silica gel (2.5% acetone/methylene chloride). Mass spec. $M^+$ 372(m+1, observed).

Step 3: N-t-Butyl-5-oxo-3,5-secoandrostan-3-oic-17β-carboxamide

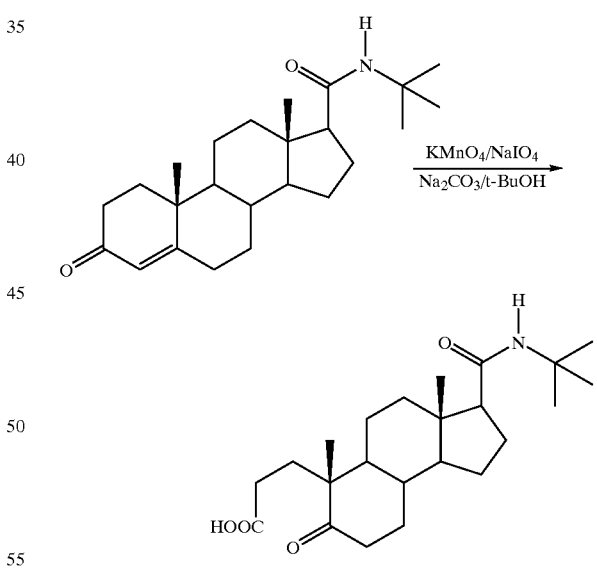

To a solution of N-t-butyl-3-oxo-androst-4-ene-17β-carboxamide (550 mg, 1.48 mmol) in t-butanol (10 mL) was added sodium carbonate (172 mg, 1.63 mmol, in 1 mL of $H_2O$). The reaction mixture was heated to 80° and a solution of $NaIO_4$ (1.58 g, 7.4 mmol) and $KMnO_4$ (11.7 mg, 0.074 mmol) in $H_2O$ (10 mL) was added dropwise in ~10 minutes. After stirring the reaction mixture for 2 hrs, the mixture was cooled to room temperature and acidified to pH 2. The reaction mixture was concentrated, extracted with ethyl acetate, organic layer was dried and concentrated to give pure product. Mass spec. $M^+$ 392(m+1, observed).

Step 4: N-t-Butyl-4-oxa-androst-5-en-3-one-17β-carboxamide

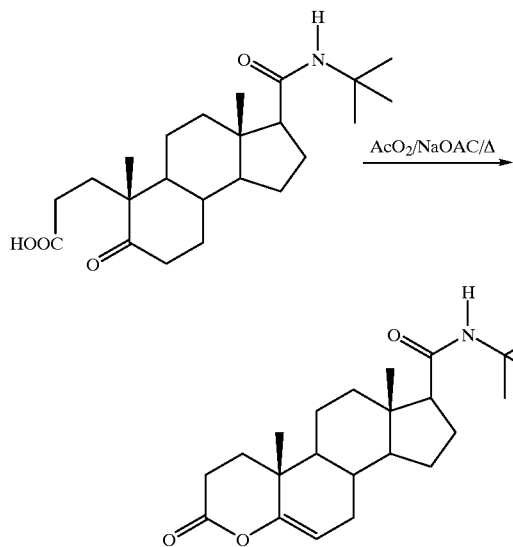

Step 6: N-t-Butyl-4-oxa-5α-androst-1-en-3-one-17β-carboxamide

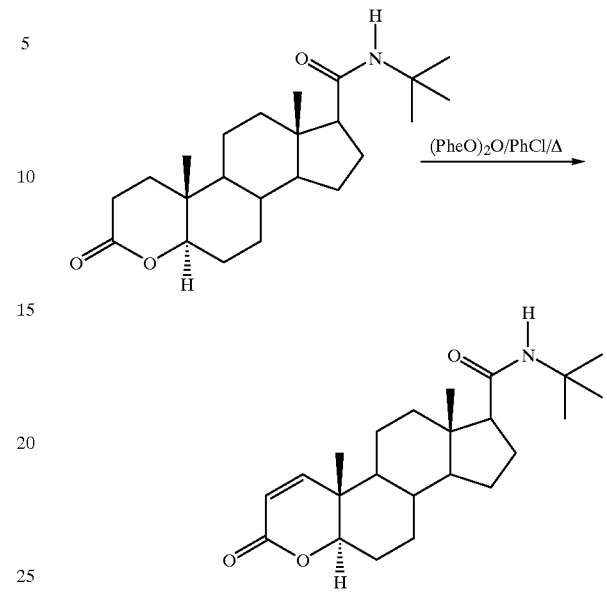

To a solution of N-t-butyl-5-oxo-3,5-secoandrostan-3-oic-17β-carboxamide (550 mg, 1.4 mmol) in acetic anhydride (25 mL) was added sodium acetate (1.91 g, 14 mmol). After stirring the reaction mixture at reflux temperature for 4 hrs, the acetic anhydride was removed under vacuum and residue partitioned between ethyl acetate and water. The organic layer was washed with brine, dried, concentrated and purified by prep. tlc (5% acetone/methylene chloride). Mass spec. $M^+$ 374(m+1, observed).

Step 5: N-t-Butyl-4-oxa-5α-androstan-3-one-17β-carboxamide

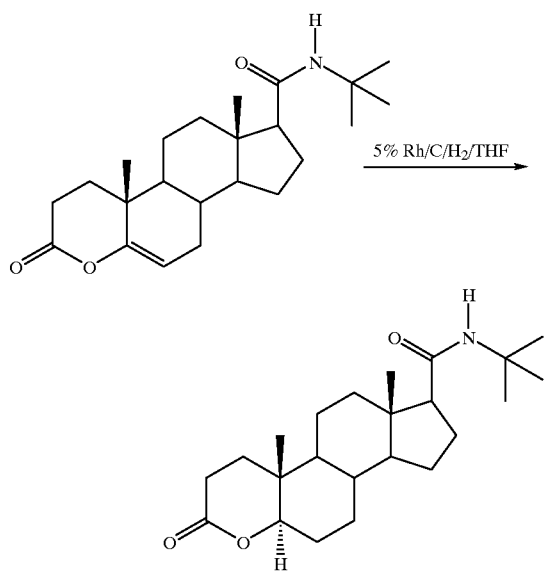

To a solution of N-t-butyl-4-oxa-androst-5-en-3-one-17β-carboxamide (410 mg, 1.099 mmol) in THF (20 mL) was added 5% Rh/C(410 mg). After stirring the reaction mixture under $H_2$ atmosphere for overnight, the mixture was flushed with $N_2$, filtered and concentrated. The residue was purified by prep. tlc (5% acetone/$CH_2Cl_2$). Mass spec. $M^+$ 376(m+1, observed).

To a solution of N-t-butyl-4-oxa-5α-androstan-3-one-17β-carboxamide (100 mg, 0.27 mmol) in chlorobenzene was added benzeneselenic anhydride (177 mg, 0.49 mmol). After stirring the reaction mixture at reflux temperature for overnight, the reaction mixture was diluted with ethyl acetate, washed with brine, dried and concentrated. The residue was purified by prep. tlc (5% acetone/$CH_2Cl_2$). Mass spec. $M^+$ 374(m+1, observed).

EXAMPLE 2

Preparation of 7β-Methyl-4-oxa-5α-Cholest-1-en-3-one

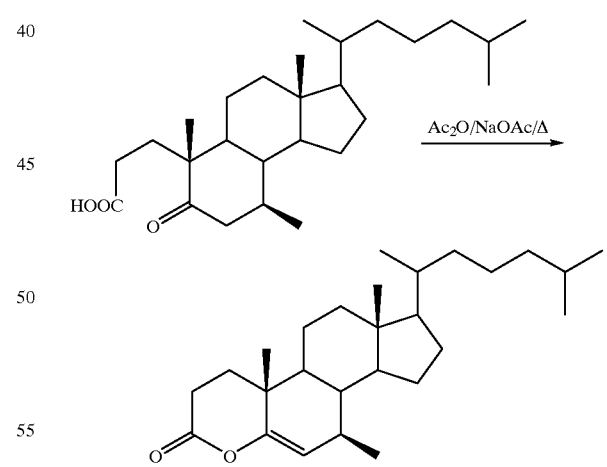

Step 1: 7β-Methyl-4-oxa-Cholest-5-en-3-one

To a solution of 7β-methyl-5-oxo-3,5-secocholestan-3-oic (5 g, 12.3 mmol) in acetic anhydride (250 mL) was added sodium acetate (16.9 g, 124 mmol). After stirring the reaction mixture at reflux temperature for 4 hrs, the acetic anhydride was removed under vacuum and residue partitioned between ethyl acetate and water. The organic layer was washed with brine, dried, concentrated and purified by chromatography over silica gel. Mass spec. $M^+$ 401(m+1, observed).

Step 2: 7β-Methyl-4-oxa-5α-Cholestan-3-one

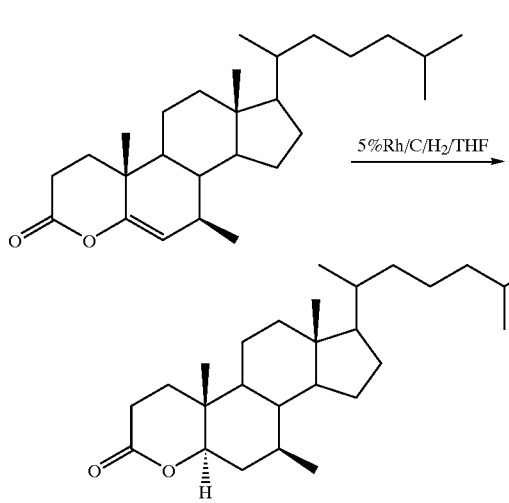

To a solution of 7β-methyl-4-oxa-Cholest-5-en-3-one (6.0 g) in THF (50 mL) was added 5% Rh/C(6.5 g). After stirring the reaction mixture under H₂ atmosphere for overnight, the mixture was flushed with N₂, filtered and concentrated. The residue was purified by chromatography over silica gel (20% ethyl acetate/hexane). Mass spec. M⁺ 403(m+1, observed).

Step 3: 7β-Methyl-4-oxa-5α-Cholest-1-en-3-one

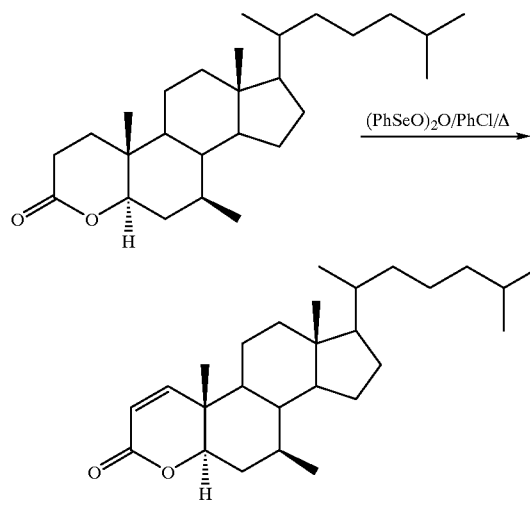

To a solution of 7β-methyl-4-oxa-5α-Cholestan-3-one (1 g, 2.49 mmol) in chlorobenzene (50 mL) was added benzeneseleninic anhydride (1.165 g, 3.24 mmol). After stirring the reaction mixture at reflux temperature for overnight, the reaction mixture was diluted with ethyl acetate, washed with brine, dried and concentrated. The residue was purified by chromatography over silica gel (10% ethyl acetate/hexane). Mass spec. M⁺ 401(m+1, observed).

EXAMPLE 3

Preparation of N-(2',5'-Bistrifluoromethylphenyl)-4-oxa-androst-1-en-3-one-17β-carboxamide Step 1: S-2'-Pyridyl-3-oxo-androst-4-ene-17β-thiocarboxylate

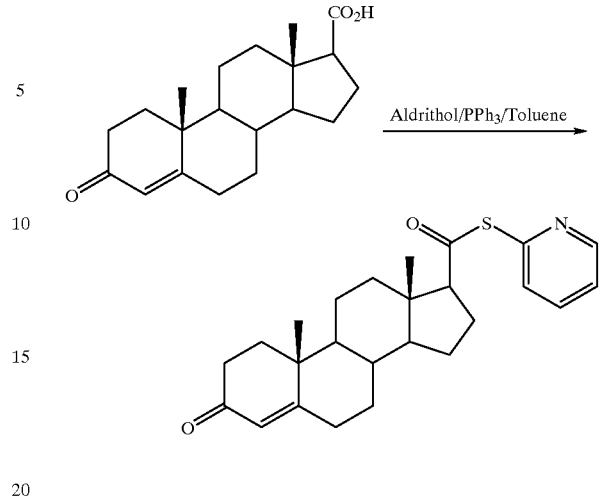

To a solution of steroid acid (10.26 g, 30 mmol) in toluene (50 mL) was added Aldrithiol (15.97 g, 72.49 mmol) and triphenylphosphine (16.88 g, 72.49 mmol). After stirring the reaction mixture for overnight at 23°, the reaction mixture was concentrated and purified by chromatography over silica gel using methylene chloride as solvent.

Step 2: N-(2',5'-Bistrifluoromethylphenyl)-3-oxo-androst-4-ene-17β-carboxamide

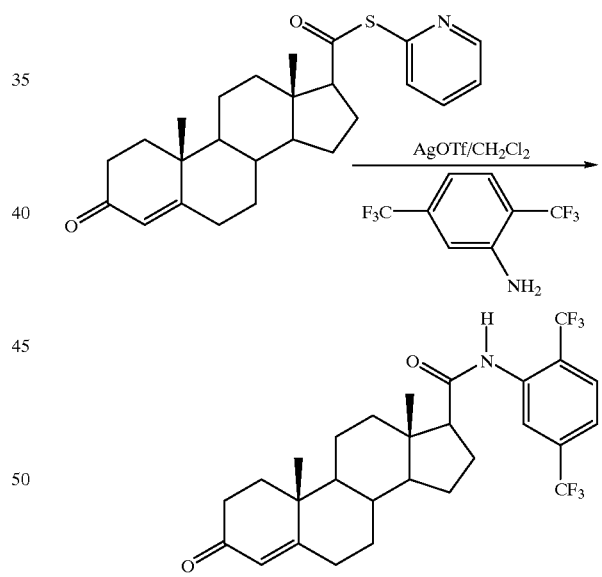

To a solution of S-2'-pyridyl-3-oxo-androst-4-ene-17β-thiocarboxylate (2.179 g, 5.19 mmol) in methylene chloride was added 2,5-bistrifluoromethylaniline (3 g, 13 mmol) and silver triflate (1.336 g, 5.2 mmol). After stirring the reaction mixture for overnight at 23°, the mixture was filtered, concentrated and purified by chromatography over silica gel using methylene chloride as solvent to give pure product.

Step 3: N-(2',5'-Bistrifluoromethylphenyl)-5-oxo-3,5-secoandrostan-3-oic-17β-carboxamide

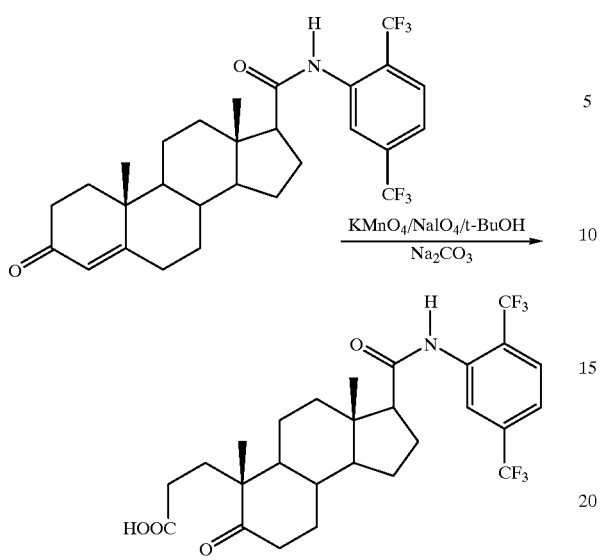

To a solution of N-(2',5'-Bistrifluoromethylphenyl)-3-oxo-androst-4-ene-17β-carboxamide (600 mg, 1.27 mmol) in t-butanol (10 mL) was added sodium carbonate (200 mg, 1.88 mmol, in 1 mL of $H_2O$). The reaction mixture was heated to 80° and a solution of $NaIO_4$ (1.81 g, 8.5 mmol) and $KMnO_4$ (13.2 mg, 0.08 mmol) in $H_2O$ (10 mL) was added dropwise in ~10 minutes. After stirring the reaction mixture for 2 hrs, the mixture was cooled to room temperature and acidified to pH 2. The reaction mixture was concentrated, extracted with ethyl acetate, organic layer was dried and concentrated to give pure product Step 4: N-(2',5'-Bistrifluoromethylphenyl)-4-oxa-androst-5-en-3-one-17β-carboxamide

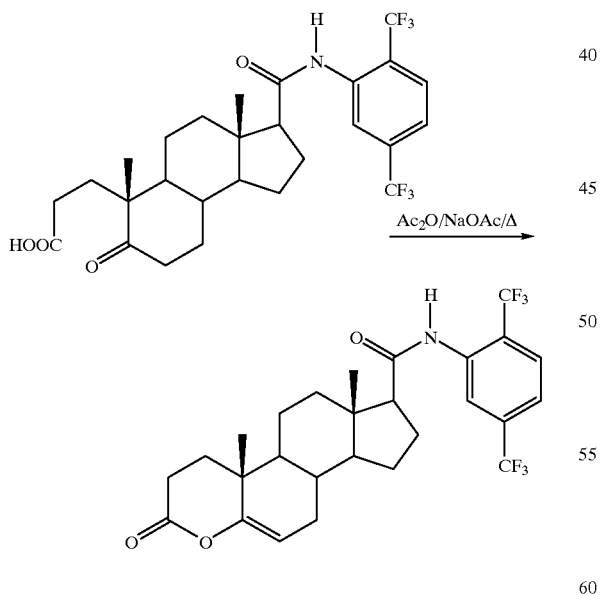

To a solution of N-(2',5'-bistrifluoromethylphenyl)-5-oxo-3,5-secoandrostan-3-oic-17β-carboxamide (600 mg, 1.19 mmol) in acetic anhydride (10 mL) was added sodium acetate (1.63 g, 11.9 mmol). After stirring the reaction mixture at reflux temperature for 4 hrs, the acetic anhydride was removed under vacuum and residue partitioned between ethyl acetate and water. The organic layer was washed with brine, dried, concentrated and purified by prep. tlc (5% acetone/methylene chloride). Mass spec. $M^+$ 530 (m+1, observed).

Step 5: N-(2',5'-Bistrifluoromethylphenyl)-4-oxa-androstan-3-one-17β-carboxamide

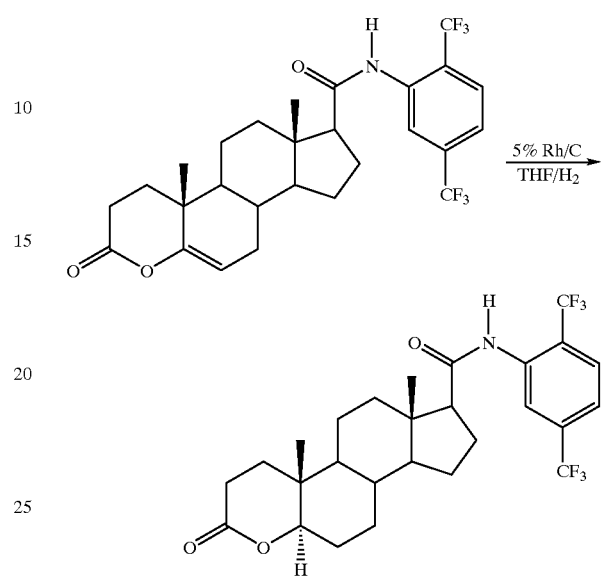

To a solution of N-(2',5'-bistrifluoromethylphenyl)-4-oxa-androst-5-en-3-one-17β-carboxamide (230 mg, 0.433 mml, prepared according to the procedures of Example 7) in THF (5 mL) was added 5% Rh/C (200 mg). After stirring the reaction mixture for overnight under hydrogen atmosphere, the reaction mixture was flushed with nitrogen, filtered, concentrated and purified by preparative tlc (50% EtOAc/hexane) to give pure product. Mass spec. $M^+$ 532 (m+1, observed).

Step 6: N-(2',5'-Bistrifluoromethylphenyl)-4-oxa-androst-1-en-3-one-17β-carboxamide

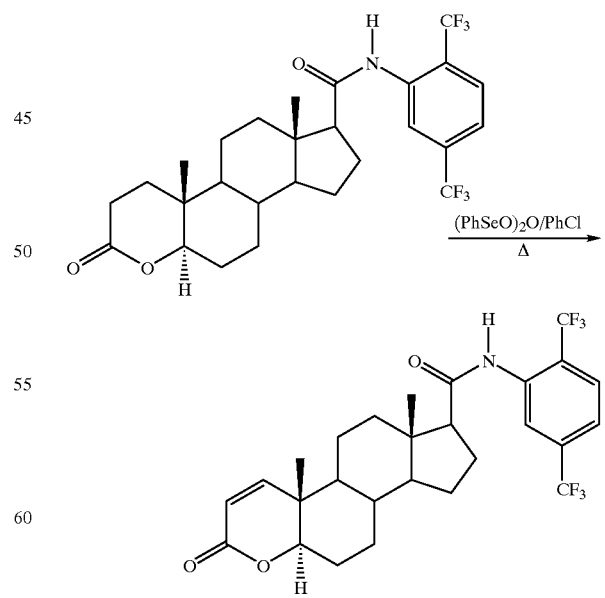

To a solution of N-(2',5'-bistrifluoromethylphenyl)-4-oxa-androstan-3-one-17β-carboxamide. (35 mg, 0.066 mmol, prepared according to the procedures of Example 8) in chlorobenzene (5 mL) was added benzeneseleninic anhydride (30 mg, 0.085 mmol). After stirring the reaction mixture at reflux temperature for overnight, the reaction mixture was diluted with ethyl acetate, washed with brine, dried and concentrated. The residue was purified by prep. tlc (50% EtOAc/hexane). Mass spec. M$^+$ 530(m+1, observed).

EXAMPLE 4

N-t-Butyl-4-thia-5α-androst-1-en-3-one-17β-carboxamide

Step 1: (N-Pyrid-3-yl)-5-hydroxy-3,5-secoandrostan-3-carboxamide-17β-(N-t-butyl)carboxamide From 500 mg of the product of step 5 of Example 1 [N-(t-butyl)-4-oxa-androstan-3-one-17β-carboxamide], the title compound is prepared by treatment with 1.25 equivalents of the dimethylaluminum complex with 3-aminopyridine by reflux in toluene for 30 min. or until the A-ring opening is shown to be complete by hplc or thin-layer chromatography. Purification is optional by column chromatography to furnish the product in good yield.

Step 2: (N-Pyrid-3-yl)-5-p-toluenesulfonyloxy-3,5-secoandrostan-3-carboxamide-17β-(N-t-butyl)carboxamide The product of step 1 in pyridine solution (50 mL) is cooled to 5° in ice before 1.2 equivalents of p-toluenesulfonyl chloride is added. After standing 18 hours in the refrigerator, the reaction is warmed to ambient temperature, partitioned between water and dichloromethane and washed with dilute bicarbonate solution to remove residual sulfonyl chloride. The organic layer is dried and evaporated to a residue, which is immediately taken on to the iodide displacement.

Step 3: (N-Pyrid-3-yl)-5-(epi)iodo-3,5-secoandrostan-3-carboxamide-17β-(N-t-butyl)carboxamide The tosyl derivative of step 2 is stirred at ambient temperature with 3 equivalents of dry tetrabutylammonium iodide in toluene for 30 min. and then heated at reflux for another 2 hrs. The reaction mixture is cooled, partitioned with dichloromethane and water, and washed to remove ammonium salts. After drying and solvent removal under reduced pressure, the residual amorphous material is chromatographed to provide the pure iodo compound.

Step 4: (N-Pyrid-3-yl)-5-acetylthio-3,5-secoandrostan-3-carboxamide-17β-(N-t-butyl)carboxamide The iodo compound of step 3 is stirred at ambient temperature with 10 equivalents of thioacetic acid in toluene for 30 min. and then heated at reflux for another 2 hrs. The reaction mixture is cooled, solvents and volatile reactants evaporated under reduced pressure, and the residual amorphous material chromatographed.

Step 5: N-t-Butyl4-thia-5α-androstan-3-one-17β-carboxamide

The thioacetyl derivative of step 4 is treated at ambient temperature with methanolic HCl (3%) until the starting material is gone by thin-layer chromatography or hplc. Product is isolated by chromatography and recrystallized.

Step 6 N-t-Butyl-4-thia-5α-androst-1-en-3-one-17β-carboxamide

Treatment of the product of step 5 with phenylseleninic anhydride by the method of step 6 of Example 1 affords the product.

EXAMPLE 5

Oral Composition

As a specific embodiment of an oral composition of a compound of this invention, 5 mg of a compound of structural formula I is formulated with sufficient finely divided lactose to provide a total amount of 580 to 590 mg to fill a size 0 hard gelatin capsule.

Biological Assays

Preparation of Human Prostatic and Scalp 5α-reductases

Samples of human tissue were pulverized using a freezer mill and homogenized in 40 mM potassium phosphate, pH 6.5, 5 mM magnesium sulfate, 25 mM potassium chloride, 1 mM phenylmethylsulfonyl fluoride, 1 mM dithiothreitol (DTT) containing 0.25 M sucrose using a Potter-Elvehjem homogenizer. A crude nuclear pellet was prepared by centrifugation of the homogenate at 1,500×g for 15 min. The crude nuclear pellet was washed two times and resuspended in two volumes of buffer. Glycerol was added to the resuspended pellet to a final concentration of 20%. The enzyme suspension was frozen in aliquots at −80° C. The prostatic and scalp reductases were stable for at least 4 months when stored under these conditions.

5α-Reductase Assay

The reaction mixture for the type 1 5α-reductase contained 40 mM potassium phosphate, pH 6.5, 5 mM [7-$^3$H]-testosterone, 1 mM dithiothreitol and 500 μM NADPH in a final volume of 100 μl. The reaction mixture for the type 2 5α-reductase contained 40 mM sodium citrate, pH 5.5, 0.3 mM [7-$^3$H]-testosterone, 1 mM dithiothreitol and 500 μM NADPH in a final volume of 100 μl. Typically, the assay was initiated by the addition of 50–100 μg prostatic homogenate or 75–200 μg scalp homogenate and incubated at 37° C. After 10–50 min. the reaction was quenched by extraction with 250 μl of a mixture of 70% cyclohexane: 30% ethyl acetate containing 10 μg each DHT and T. The aqueous and organic layers were separated by centrifugation at 14,000 rpm in an Eppendorf microfuge. The organic layer was subjected to normal phase HPLC (10 cm Whatman partisil 5 silica column equilibrated in 1 mL/min 70% cyclohexane: 30% ethyl acetate; retention times: DHT, 6.8–7.2 min.; androstanediol, 7.6–8.0 min.; T, 9.1–9.7 min.). The HPLC system consisted of a Waters Model 680 Gradient System equipped with a Hitachi Model 65560 autosampler, Applied Biosystems Model 757 variable UV detector, and a Radiomatic Model A120 radioactivity analyzer. The conversion of T to DHT was monitored using the radioactivity flow detector by mixing the HPLC effluent with one volume of Flo Scint 1 (Radiomatic). Under the conditions described, the production of DHT was linear for at least 25 min. The only steroids observed with the human prostate and scalp preparations were T, DHT and androstanediol.

Inhibition Studies

Compounds were dissolved in 100% ethanol. The compound to be tested was pre-incubated with the enzyme (either 5α-reductase type 1 or 2) prior to initiation by addition of substrate testosterone. IC$_{50}$ values represent the concentration of inhibitor required to decrease enzyme conversion of testosterone to dihydrotestosterone by 50% of the control. IC$_{50}$ values were determined using a 6 point titration where the concentration of the inhibitor was varied from 0.1 to 1000 nM. Representative compounds of this invention were tested in the above described assay for 5α-reductase type 1 and type 2 inhibition.

A compound referred to herein as a 5α-reductase 1 inhibitor is a compound that shows inhibition of the 5α-reductase 1 isozyme in the above-described assay, having an IC$_{50}$ value of about or under 100 nM.

A compound referred to herein as a 5α-reductase 2 inhibitor is a compound that shows inhibition of the 5α-reductase 2 isozyme in the above-described assay, having an IC$_{50}$ value of about or under 100 nM.

Human Dermal Papilla Cell Assay

The dermal papilla is a small group of cells at the base of each hair follicle, and it is presently thought that these cells are stem cells that form the basis for hair growth. These cells have been shown to have 5α reductase activity, and it is therefore possible to test inhibitors of 5α reductase in these cell culture systems.

Isolated and cultured dermal papilla cells are prepared according to the methods of Messenger, A. G., "The Culture of Dermal Papilla Cells From Human Hair Follicles," *Br. J. Dermatol.*, 110:685–689 (1984) and Itami, S. et al., "5α-Reductase Activity In Cultured Human Dermal Papilla Cells From Beard Compared With Reticular Dermal Fibroblasts," *J. Invest. Dermatol.*, 94:150–152 (1990). Beard dermal papilla cells and occipital scalp hair of two different individuals are used throughout the study. All experiments are performed at confluency after the fourth to sixth subculture. Confluent monolayers are rinsed twice with phosphate-buffered saline, scraped from dishes by rubber policemen, and collected into a centrifuge tube. The cell suspensions are centrifuged at 1,500 rpm for 10 min. at 4° C. The pellets are resuspended in 20 mM Tris-HCl buffer, pH 7.5, at 4° C., containing 250 mM sucrose, 1 mM $MgCl_2$, and 2 mM $CaCl_2$, by vortexing and 10 passes through a 25-gauge needle. The crude homogenate is further homogenized by a teflon-glass homogenizer, and is used as the cell homogenate. For the study of subcellular localization of 5α-reductase, the cell homogenate is centrifuged at 800×g for 10 min. to yield a crude nuclear pellet. The resultant supernatant is centrifuged at 10,000×g for 15 min. to produce a crude mitochondrial pellet. The supernatant is centrifuged at 100,000×g for 60 min. to yield a microsomal pellet and cytosol. Each particulate fraction is washed twice and resuspended in the buffer.

A standard incubation mixture will consist of 50 nM [$^3$H]-testosterone, 1 mM NADPH, 100 mM sodium citrate, pH 5.5 or 100 mM Tris-HCl, pH 7.5, and 50 mL of the cell homogenate, in a final volume of 100 mL. Each tube contains 50–100 mg of cellular protein. Incubation is carried out at 37° C. for 30 min. During this incubation, the reaction is proportional to the time. For the study of optimum pH, citrate buffer is used at pH 4.5–6.5, and the Tris HCl buffer at pH 7.0–9.0. The protein content is determined by the method of Lowry, et al., "Protein Measurement With The Folin Phenol Reagent," *J. Biol. Chem.*, 193:265–275 (1951).

After incubation, the reaction is stopped by adding 4 times volume of chloroform-methanol (2/1:V/V) containing 110 mg each of carrier steroids. The extracted steroids are analyzed by thinlayer chromatography as previously described by Gomez, et al., "In Vitro Metabolism Of Testosterone-4-$^{14}$C and D-androstene-3, 17-dione-4-$^{14}$C In Human Skin.," *Biochem.*, 7:24–32 (1968), and the purity of each steroid is determined by the recrystallization method. The activity of 5α-reductase is expressed by the sum of dihydrotestosterone, androstanediol and androstanedione formed. [1,2-$^3$H]-testosterone (55.2 Ci/mmol) is obtainable from New England Nuclear Corporation (Boston, Mass.) and unlabeled steroids can be purchased from Sigma Chemical Company (St. Louis, Mo.). Fetal calf serum is obtainable from Hazleton (Lenaxa, Kans.). All other chemicals are of reagent grade.

The following describes an example of methodology that can be used for detection of hair growth.

Macrophotography and Global Photography Procedure for Detection of Hair Growth

A. Macrophotographic Procedure

Location:
 ID card
 Haircount target area
Equipment:
Film:
 Kodak-T-max 24 exposure each of same emulsion lot number
Camera:
 Nikon N-6000
Lens:
 Nikkor 60 mm f2.8
Flashes:
 Nikon SB-21B Macroflash
Device:
 registration device
Photographic Procedure In these clinical photographs, the only variable allowed is the haircount. Film emulsion, lighting, framing, exposure, and reproduction ratios are held constant.

1. The haircount area on the patient is prepared as follows: A small (~1 mm) dot tattoo is placed at the beginning of the study at the leading edge of the bald area directly anterior to the center of the vertex bald spot, using a commercial tattooing machine or manually (needle and ink). An area approximately one square inch in size, centered at the tattoo at the leading edge of the balding area, is clipped short (~2 mm). Cut hairs are removed from the area to be photographed, using tape. Compressed air and/or ethanol wipes may also be used to facilitate removal of cut hairs.

2.
Magnification:
 Each lens supplied has a fixed reproduction ratio of 1:1.2.
Aperture:
 Every photograph is taken at f/22.
Film:
 T-Max 100 (24 exposure) is used.

3. Patient's haircount target area. Three exposures (−2/3, 0, and +2/3 f-stop).

A trained technician places a transparency over the photographic print and, using a felt tip pen, places a black dot over each visible hair. The dot map transparency is then counted using image analysis with computer assistance.

Photographs are coded with a random number corresponding to study site, visit number and patient allocation number to insure blinding to time. At Month 6, baseline and Month 6 photographs are counted and data analyzed for interim analysis. At Month 12, baseline, Month 6 and Month 12 photographs are counted and data analyzed for the primary endpoint.

Methodology for detection of hair growth is also described in Olsen, E. A. and DeLong, E., *J. American Academy of Dermatology*, Vol. 23, p. 470 (1990).

B. Global Photographic Procedure

Locations:
 Color card/patient Id
 Global photograph
Equipment:
Film:
 Kodachrome KR-64 24 exposure each of same emulsion lot number
Camera:
 Nikon N-6000

Lens:
 Nikkor 60 mm f2.8
Flashes:
 Nikon SB-23
Photographic Procedure

In these clinical photographs, the only variable allowed is the global area's appearance. Anything extraneous to the area (clothing, furniture, walls, etc.) is eliminated from the fields to be photographed.

1. Patients will have global photographs taken prior to hair clipping with the head in a fixed position (determined by the supplied stereotactic device). Hair on the patient's head is positioned consistently so as to not obscure the bald area.

2. Magnification: Each lens supplied has a fixed reproduction ratio of 1:6.

Aperture:
 Every photograph will be taken at f/11.
Film:
 Kodachrome (24 exposure) is used.

3. Patient's global photographs. Three exposures at zero compensation.

While the invention has been described and illustrated with reference to certain particular embodiments thereof, those skilled in the art will appreciate that various changes, modifications and substitutions can be made therein without departing from the spirit and scope of the invention. For example, effective dosages other than the particular dosages as set forth herein above may be applicable as a consequence of variations in the responsiveness of the mammal being treated for any of the indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of structural formula (I):

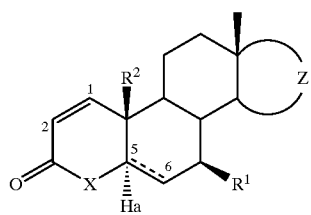

(I)

or a pharmaceutically acceptable salt, ester or stereoisomer thereof, wherein:

the C5–C6 bond designated with a dotted line independently represents a single or double bond, provided that when the C5–C6 is a double bond, $H_a$ is absent and when the C5–C6 bond is a single bond $H_a$ is present and represents hydrogen;

X is sulfur;

$R^1$ is selected from hydrogen and $C_{1-5}$ alkyl;

$R^2$ is selected from $CH_3$, $CH_2OR^3$, and H;

$R^3$ is selected from: $C_{1-5}$ alkyl;

Z is

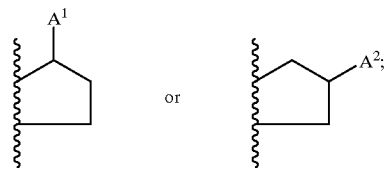

$A^1$ is selected from:
(1) —H,
(2) keto,
(6) carboxy,
(7) protected amino,
(8) amino,
(9) substituted or unsubstituted $C_{2-10}$alkenyl,
(10) aryl-substituted $C_{1-10}$ alkyl,
(11) aryl or heteroaryl,
(12) substituted aryl or heteroaryl,
(13) aryl or heteroaryl carbamoyl-substituted $C_{1-10}$alkyl,
(14) aryl or heteroaryl carbonyl,
(15) ether-substituted $C_{1-10}$alkyl,
(16) thioether-substituted $C_{1-10}$alkyl,
(17) keto-substituted $C_{1-10}$alkyl,
(18) heteroaryl-substituted $C_{1-10}$ alkyl,
(19) carboxylic ester,
(20) carboxamide, including substituted and unsubstituted anilide derivatives,
(21) urea,
(22) $C_{1-10}$ alkylureido $C_{0-5}$ alkyl,
(23) substituted or unsubstituted heteroaryl or arylureido$C_{0-5}$ alkyl,
(24) $C_{1-10}$alkanoyloxy$C_{1-2}$alkyl,
(25) $C_{1-10}$ alkylcarbonylamino,
(26) alkanoylamidoalkyl
(28) ether,
(29) thio ether, and
(30) substituted and unsubstituted aryl or heteroaryl ether;

$A^2$ is selected from:
(1) —H,
(2) keto,
(3) protected hydroxy,
(4) acetate,
(5) hydroxy,
(6) carboxy,
(7) protected amino,
(8) amino,
(9) $C_{1-10}$ alkyl,
(10) substituted or unsubstituted $C_{2-10}$alkenyl,
(11) aryl-substituted $C_{1-10}$ alkyl,
(12) aryl or heteroaryl,
(13) substituted aryl or heteroaryl,
(14) aryl or heteroaryl carbamoyl-substituted $C_{1-10}$alkyl,
(15) $C_{1-10}$alkylcarbonyl,
(16) aryl or heteroaryl carbonyl,
(17) ether-substituted $C_{1-10}$alkyl,
(18) thioether-substituted $C_{1-10}$alkyl,
(19) keto-substituted $C_{1-10}$alkyl,
(20) heteroaryl-substituted $C_{1-10}$ alkyl,
(21) carboxylic ester,

(22) carboxamide, including substituted and unsubstituted anilide derivatives,
(23) urea,
(24) $C_{1-10}$ alkylureido $C_{0-5}$ alkyl,
(25) substituted or unsubstituted arylureido$C_{0-5}$ alkyl,
(26) $C_{1-10}$alkanoyloxy$C_{1-2}$alkyl,
(27) $C_{1-10}$ alkylcarbonylamino,
(28) alkanoylamidoalkyl,
(29) ether,
(30) thio ether, and
(31) substituted and unsubstituted aryl- or heteroaryl-ether; and heteroaryl is selected from: piperidinyl, piperizinyl, pyrrolidinyl, pyrrolyl, furanyl, thienyl, pyridyl, pyrimidinyl, indolyl and benzofuranyl.

2. The compound of claim 1 wherein:

(a) protected hydroxy is selected from: dimethyl-t-butyl silyloxy, trimethylsilyloxy, tri-ethylsilyloxy, tri-isopropylsilyloxy, and triphenylsilyloxy;

(b) protected amino is acetylamino, benzoylamino, and pivaloylamino;

(c) $C_{1-10}$ alkyl is selected from methyl, ethyl, propyl, butyl, pentyl, 1,5-dimethylhexyl, 6-methylhept-2-yl, and 1-methyl-4-isopropylhexyl;

(d) aryl substituted $C_{1-10}$ alkyl is omegaphenylpropyl;

(e) aryl is selected from phenyl, and naphthyl;

(f) substituted aryl or heteroaryl is selected from phenyl, pyridyl and pyrimidinyl substituted with one to three substituents independently selected from:
(1) —H,
(2) —OH,
(3) —CH$_3$,
(4) —OCH$_3$,
(5) —S(O)$_n$—CH$_3$, wherein n is selected from 0, 1, and 2,
(6) —CF$_3$,
(7) halo,
(8) —CHO,
(9) CN,
(10) phenyloxy,
(11) ethyl,
(12) t-butyl,
(13) OCH$_2$CH$_3$,
(14) OC(CH$_3$)$_3$, and
(15) —NHR$^7$, wherein R$^7$ is selected from:
—H, —C$_{1-8}$ alkyl, —C$_{1-6}$ alkylcarbonyl, —C$_{1-6}$ alkylsulfonyl, and —C$_{1-6}$ alkoxycarbonyl, (g) aryl or heteroaryl carbamoyl substituted $C_{1-10}$ alkyl is 2-(4-pyridyl-carbamoyl)ethyl;

(h) $C_{1-10}$alkylcarbonyl is selected from isobutylcarbonyl and isopropylcarbonyl;

(i) aryl or heteroaryl carbonyl is selected from phenylcarbonyl and pyridyl carbonyl;

(j) ether-substituted $C_{1-10}$alkyl is selected from 1-methoxy-ethyl and 1-ethoxy-ethyl;

(k) thioether-substituted $C_{1-10}$alkyl is selected from 1-methylthio-ethyl, and 1-ethylthio-ethyl;

(l) keto-substituted $C_{1-10}$alkyl is 1-keto-ethyl, ketomethyl, 1-ketopropyl, and ketobutyl;

(m) heteroaryl-substituted $C_{1-10}$ alkyl is omega-(4-pyridyl)butyl;

(n) carboxylic esters are $C_{1-10}$ alkylcarboxylic esters selected from carbomethoxy and carboethoxy;

(o) carboxamides are selected from N,N-diisopropyl carboxamide, N-t-butyl carboxamide, N-t-octyl carboxamide, N-n-octyl carboxamide, N-(hydroxyphenyl)carboxamide, N-phenylcarboxamide, N-(aminophenyl)carboxamide, N-(carbomethoxy)phenyl carboxamide, N-(methoxycarboxy)phenyl carboxamide, N-acetamidophenyl-N-acetyl-carboxamide, N-acetamidophenyl-carboxamide, N-pivalamidophenyl carboxamide, N-isobutyramidophenyl carboxamide, N-(methyl),N-diphenylmethyl)carboxamide, N-(diphenylmethyl)-carboxamide, N-t-butyl carboxamide, N-isopropyl carboxamide, 1-adamantyl carboxamide, 2-adamantyl carboxamide and N-(substituted phenyl)carboxamides wherein the phenyl may be substituted with 1 to 2 substitutents selected from ethyl, methyl, trifluoromethyl or halo (F, Cl, Br, I);

(p) $C_{1-10}$alkanoyloxy$C_{1-2}$alkyl is selected from acetyloxymethyl, trimethylacetyloxymethyl, and (2-ethylhexanoyloxy)methyl;

(q) urea is t-butylcarbonylamino urea;

(r) $C_{1-10}$ alkylureido $C_{0-5}$ alkyl is selected from: N-t-butylureidomethyl, N-n-propylureidomethyl, N-n-octylureidomethyl and, N-isopropylureido, (s) substituted or unsubstituted arylureido$C_{0-5}$ alkyl is selected from: N-(ethylphenyl)ureidomethyl, N-(chlorophenyl)ureidomethyl, N-phenylureidomethyl, N-(dichlorophenyl) ureidomethyl, N-(naphth-2-yl)ureidomethyl, N-(fluorophenyl)ureido, N-(methoxyphenyl)ureido, and 2-(ethoxyphenyl)ureidomethyl;

(t) $C_{1-10}$ alkylcarbonylamino is t-butylcarbonylamino;

(u) alkanoylamidoalkyl is selected from: trimethylacetamidomethyl, carbomethoxyoctanoylamidomethyl, (isobutylphenyl) propionamidomethyl, 8-carboxyoctanoylamidomethyl, bromoheaxanoylamido methyl, hydroxydodecanoyl amidomethyl, 4-nitrophenylprionamidomethyl, isopropylthioacetamidomethyl, benzyloxyacetamidomethyl, carbomethoxyacetamidomethyl, triphenylproprionamidomethyl, cyclohexylacetamidomethyl, methylcyclohexanecarboxamidomethyl, (3-hydroxy-4,4,4-trichlorobutyramido)methyl, and phenylthioacetamidomethyl;

(u) ether is $C_{1-8}$alkyl ether optionally substituted with hydroxy, halo, $C_{1-8}$alkoxy, $C_{2-6}$alkenyl, or aryl;

(w) thioether is selected from: $C_{1-8}$alkylthio, phenylthio, and $C_{1-8}$ alkylthio substituted with phenyl; and (x) substituted and unsubstituted aryl or heteroaryl ether is selected from thiophenoxy, biphenyloxy, acetamidophenoxy, (3-pyridyl)oxy, chlorophenyloxy, methylphenyloxy, phenoxy, hydroxyphenyloxy, methylsulfonylphenyloxy and pyrimidinyloxy.

3. The compound of claim 1 wherein Z is:
Z is

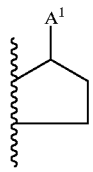

4. The compound of claim 3 wherein:
R$^1$ is hydrogen, R$^2$ is selected from H and CH$_3$, and A$^1$ is carboxamide.

5. The compound of claim 4 wherein carboxamide is selected from:
N,N-diisopropyl carboxamide,
N-t-butyl carboxamide,
N-t-octyl carboxamide,
N-n-octyl carboxamide,
N-(hydroxyphenyl)carboxamide,
N-phenylcarboxamide,
N-(aminophenyl)carboxamide,
N-(carbomethoxy)phenyl carboxamide,
N-(methoxycarboxy)phenyl carboxamide,
N-acetamidophenyl-N-acetyl-carboxamide,
N-acetamidophenyl-carboxamide,
N-pivalamidophenyl carboxamide,
N-isobutyramidophenyl carboxamide,
N-(methyl),N-diphenylmethyl)carboxamide,
N-(diphenylmethyl)-carboxamide,
N-t-butyl carboxamide,
N-isopropyl carboxamide,
1-adamantyl carboxamide,
2-adamantyl carboxamide, and
N-(substituted phenyl)carboxamides, wherein:
   the phenyl may be substituted with 1 to 2 substitutents selected from ethyl, methyl, trifluoromethyl or halo (F, Cl, Br, I).

6. The compound of claim 5 wherein carboxamide is selected from: —C(=O)NH—C(CH$_3$)$_3$, —C(=O)NH—C$_6$H$_5$ and —C(=O)NH—(2,5-trifluoromethylphenyl).

7. The compound of claim 3, wherein:
R$^1$ is CH$_3$, R$^2$ is selected from H and CH$_3$, and A$^1$ is carboxamide.

8. The compound of claim 7 wherein carboxamide is selected from —C(=O)NH—C$_6$H$_5$ and —C(=O)NH-(2,5-trifluoromethylphenyl).

9. The compound of claim 1 wherein Z is

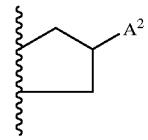

10. The compound of claim 9 wherein R$^1$ is H or CH$_3$, R$^2$ is selected from H and CH$_3$, and A$^2$ is selected from: aryl ether and heteroaryl ether, either unsubstituted or substituted with one to three substituents independently selected from:

(1) —H,
(2) —OH,
(3) —CH$_3$,
(4) —OCH$_3$,
(5) —S(O)$_n$—CH$_3$, wherein n is selected from 0, 1, and 2,
(6) —CF$_3$,
(7) halo,
(8) —CHO,
(9) CN,
(10) phenyloxy,
(11) ethyl,
(12) t-butyl,
(13) OCH$_2$CH$_3$,
(14) OC(CH$_3$)$_3$, and
(15) —NHR$^7$, wherein R$^7$ is selected from: —H, —C$_{1-8}$ alkyl, —C$_{1-6}$ alkylcarbonyl, —C$_{1-6}$ alkylsulfonyl, and —C$_{1-6}$ alkoxycarbonyl.

11. The compound of claim 10 wherein substituted and unsubstituted aryl or heteroaryl ether is selected from thiophenoxy, biphenyloxy, acetamidophenoxy, (3-pyridyl)oxy, chlorophenyloxy, methylphenyloxy, phenoxy, hydroxyphenyloxy, methylsulfonylphenyloxy and pyrimidinyloxy.

12. A pharmaceutical composition comprising a pharmaceutically acceptable carrier and a therapeutically effective amount of a compound of claim 1.

13. The compound selected from:
(1) N-t-Butyl-4-thia-5α-androst-1-en-3-one-17β-carboxamide,
(2) 7β-Methyl-4-thia-5α-cholest-1-en-3-one,
(3) 17β-(2,5-bis(trifluoromethyl)phenylcarbamoyl)-4-thia-5α-androst-1-en-3-one,
(4) 17β-(2,3-bis(trifluoromethyl)phenylcarbamoyl)-4-thia-5α-androst-1-en-3-one,
(5) 17β-(2,4-bis(trifluoromethyl)phenylcarbamoyl)-4-thia-5α-androst-1-en-3-one,
(6) 17β-(2,6-bis(trifluoromethyl)phenylcarbamoyl)-4-thia-5α-androst-1-en-3-one,
(7) 17β-(N-tert-amylcarbamoyl)-4-thia-5α-androst-1-en-3-one,
(8) 17β-(N-tert-hexylcarbamoyl)-4-thia-5α-androst-1-en-3-one,
(9) 17β-(N-isobutylcarbamoyl)-4-thia-5α-androst-1-en-3-one,
(10) 17β-(N-tert-octylcarbamoyl)-4-thia-5α-androst-1-en-3-one,
(11) 17β-(N-1,1-diethylbutylcarbamoyl)-4-thia-5α-androst-1-en-3-one,
(12) 17β-(N-neopentylcarbamoyl)-4-thia-5α-androst-1-en-3-one,
(13) 17β-(N-2-adamantylcarbamoyl)-4-thia-5α-androst-1-en-3-one,
(14) 17β-(N-1-adamantylcarbamoyl)-4-thia-5α-androst-1-en-3-one,
(15) 17β-(N-2-norbornylcarbamoyl)-4-thia-5α-androst-1-en-3-one,
(16) 17β-(N-1-norbornylcarbamoyl)-4-thia-5α-androst-1-en-3-one,
(17) 17β-(N-phenylcarbamoyl)-4-thia-5α-androst-1-en-3-one,
(18) 17β-(N-benzylcarbamoyl)-4-thia-5α-androst-1-en-3-one,

(19) 17β-(2,3-bis(trifluoromethyl)phenylcarbamoyl)-7β-methyl-4-thia-5α-androst-1-en-3-one,
(20) 17β-(2,4-bis(trifluoromethyl)phenylcarbamoyl)-7β-methyl-4-thia-5α-androst-1-en-3-one,
(21) 17β-(2,6-bis(trifluoromethyl)phenylcarbamoyl)-7β-methyl-4-thia-5α-androst-1-en-3-one,
(22) 17β-(N-n-octylcarbamoyl)-4-methyl-4-thia-5α-androst-1-en-3-one,
(23) 17β-(1-methoxyethyl)-7β-methyl-4-thia-5α-androst-1-en-3one,
(24) 17β-(isopropyl)-7β-methyl-4-thia-5α-androst-1-en-3-one,
(25) 17β-(4-methyl-phenoxy)-7β-methyl-4-thia-5α-androst-1-en-3-one,
(26) 17β-(1-(3-chlorophenoxy)ethyl)-7β-methyl-4-thia-5α-androst-1-en-3-one,
(27) 17β-(4-methylsulfonyl-phenoxy)-7β-methyl-4-thia-5α-androst-1-en-3-one,
(28) 17β-(4-chlorophenoxy)-7β-methyl-4-thia-5α-androst-1-en-3-one,
(29) 17β-(2-pyrimidinyloxy)-7β-methyl-4-thia-5α-androst-1-en-3-one,
(30) 17β-(2,5-bis(trifluoromethyl)phenylcarbamoyl)-7β-methyl-4-thia-5α-androst-1-en-3-one,
(31) N-t-Butyl-4-thia-5α-androst-1-en-3-one-16β-carboxamide,
(32) 16β-(1,5-dimethylhexyl)-7β-Methyl-4-thia-5α-androst-1-en-3-one,
(33) 16β-(2,5-bis(trifluoromethyl)phenylcarbamoyl)-4-thia-androst-1-en-3-one,
(34) 16β-(N-tert-amylcarbamoyl)-4-thia-5α-androst-1-en-3-one,
(35) 16β-(N-tert-hexylcarbamoyl)-4-thia-5α-androst-1-en-3-one,
(36) 16β-(N-isobutylcarbamoyl)-4-thia-5α-androst-1-en-3-one,
(37) 16β-(N-tert-octylcarbamoyl)-4-thia-5α-androst-1-en-3-one,
(38) 16β-(N-1,1-diethylbutylcarbamoyl)-4-thia-5α-androst-1-en-3-one,
(39) 16β-(N-neopentylcarbamoyl)-4-thia-5α-androst-1-en-3-one,
(40) 16β-(N-2-adamantylcarbamoyl)-4-thia-5α-androst-1-en-3-one,
(41) 16β-(N-1-adamantylcarbamoyl)-4-thia-5α-androst-1-en-3-one,
(42) 16β-(N-2-norbomylcarbamoyl)-4-thia-5α-androst-1-en-3-one,
(43) 16β-(N-1-norbomylcarbamoyl)-4-thia-5α-androst-1-en-3-one,
(44) 16β-(N-phenylcarbamoyl)-4-thia-5α-androst-1-en-3-one,
(45) 16β-(N-benzylcarbamoyl)-4-thia-5α-androst-1-en-3-one,
(46) 16β-(2,3-bis(trifluoromethyl)phenylcarbamoyl)-7β-methyl-4-thia-5α-androst-1-en-3-one,
(47) 16β-(2,4-bis(trifluoromethyl)phenylcarbamoyl)-7β-methyl-4-thia-5α-androst-1-en-3one,
(48) 16β-(2,6-bis(trifluoromethyl)phenylcarbamoyl)-7β-methyl-4-thia-5α-androst-1-en-3-one,
(49) 16β-(2,3-bis(trifluoromethyl)phenylcarbamoyl)-4-thia-androst-1-en-3-one,
(50) 16β-(2,4-bis(trifluoromethyl)phenylcarbamoyl)-4-thia-androst-1-en-3-one,
(51) 16β-(2,6-bis(trifluoromethyl)phenylcarbamoyl)-4-thia-androst-1-en-3-one,
(52) 16β-(N-n-octylcarbamoyl)-4-methyl-4-thia-5α-androst-1-en-3-one,
(53) 16β-(1-methoxyethyl)-7β-methyl-4-thia-5α-androst-1-en-3-one,
(54) 16β-(isopropyl)-7β-methyl-4-thia-5α-androst-1-en-3-one,
(55) 16β-(4-methyl-phenoxy)-7β-methyl-4-thia-5α-androst-1-en-3-one,
(56) 16β-(1-(3-chlorophenoxy)ethyl)-7β-methyl-4-thia-5α-androst-1-en-3-one,
(57) 16β-(4-methylsulfonyl-phenoxy)-7β-methyl-4-thia-5α-androst-1-en-3-one,
(58) 16β-(4-chlorophenoxy)-7β-methyl-4-thia-5α-androst-1-en-3-one,
(59) 16β-(2-pyrimidinyloxy)-7β-methyl-4-thia-5α-androst-1-en-3-one, and
(60) 16β-(2,5-bis(trifluoromethyl)phenylcarbamoyl)-7β-methyl-4-thia-5α-androst-1-en-3-one.

14. The compound of claim 13 selected from:
(1) N-t-Butyl-4-thia-5α-androst-1-en-3-one-17β-carboxamide,
(2) 7β-Methyl-4-thia-5α-cholest-1-en-3-one,
(3) 17β-(2,5-bis(trifluoromethyl)phenylcarbamoyl)-4-thia-androst-1-en-3-one,
(4) 17β-(N-phenylcarbamoyl)-4-thia-5α-androst-1-en-3-one,
(5) 17β-(N-benzylcarbamoyl)-4-thia-5α-androst-1-en-3-one,
(6) 17β-(1-methoxyethyl)-7β-methyl-4-thia-5α-androst-1-en-3-one,
(7) 17β-(isopropyl)-7β-methyl-4-thia-5α-androst-1-en-3-one,
(8) 17β-(4-methylphenoxy)-7β-methyl-4-thia-5α-androst-1-en-3-one,
(9) 17β-(1-(3-chlorophenyoxy)ethyl)-7β-methyl-4-thia-5α-androst-1-en-3-one,
(10) 17β-(4-methylsulfonyl-phenoxy)-7β-methyl-4-thia-5α-androst-1-en-3-one,
(11) 17β-(methyl-phenoxy)-7β-methyl-4-thia-5α-androst-1-en-3-one,
(12) 17β-(4-chlorophenoxy)-7β-methyl-4-thia-5α-androst-1-en-3-one,
(13) 17β-(2-pyrimidinyloxy)-7β-methyl-4-thia-5α-androst-1-en-3-one,
(14) 17β-(2,5-bis(trifluoromethyl)phenylcarbamoyl)-7β-methyl-4-thia-5α-androst-1-en-3-one,
(15) 16β-(4-methyl-phenoxy)-7β-methyl-4-thia-5α-androst-1-en-3-one,
(16) 16β-(1-(3-chlorophenoxy)ethyl)-7β-methyl-4-thia-5α-androst-1-en-3-one,
(17) 16β-(4-methylsulfonyl-phenoxy)-7β-methyl-4-thia-5α-androst-1-en-3-one,
(18) 16β-(4-chlorophenoxy)-7β-methyl-4-thia-5α-androst-1-en-3-one, and
(19) 16β-(2-pyrimidinyloxy)-7β-methyl-4-thia-5α-androst-1-en-3-one.

* * * * *